United States Patent
Yohanan et al.

(10) Patent No.: US 9,757,229 B2
(45) Date of Patent: *Sep. 12, 2017

(54) PROSTHETIC HEART VALVE HAVING IMPROVED COMMISSURE SUPPORTS

(71) Applicant: Edwards Lifesciences Corporation, Irvine, CA (US)

(72) Inventors: Ziv Yohanan, Yesud Hamaala (IL); Tamir S. Levi, Moshav Ein HaEmek (IL); Netanel Benichou, D.N. Hof HaCarmel (IL); Michael Bukin, Pardes Hana (IL); Nikolay Gurovich, Hadera (IL); Elena Sherman, Pardes Hanna (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/922,057

(22) Filed: Oct. 23, 2015

(65) Prior Publication Data

US 2016/0045307 A1    Feb. 18, 2016

Related U.S. Application Data

(63) Continuation of application No. 13/708,598, filed on Dec. 7, 2012, now Pat. No. 9,168,131.
(Continued)

(51) Int. Cl.
*A61F 2/24*    (2006.01)

(52) U.S. Cl.
CPC .......... *A61F 2/2409* (2013.01); *A61F 2/2412* (2013.01); *A61F 2/2418* (2013.01);
(Continued)

(58) Field of Classification Search
CPC .................................... A61F 2/24; A61F 2/82
(Continued)

(56) References Cited

U.S. PATENT DOCUMENTS

| | | | |
|---|---|---|---|
| 3,409,013 A | 11/1968 | Berry | |
| 3,472,230 A | 10/1969 | Fogarty | |

(Continued)

FOREIGN PATENT DOCUMENTS

| | | | |
|---|---|---|---|
| DE | 2246526 A1 | 3/1973 | |
| DE | 19532846 A1 | 3/1997 | |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Suzette J Gherbi
(74) *Attorney, Agent, or Firm* — Klarquist Sparkman LLP; Thomas C. Richardson

(57) ABSTRACT

A prosthetic heart valve according to the present disclosure comprises a radially collapsible and expandable annular frame and a leaflet structure comprising a plurality of leaflets mounted within the frame. The frame in particular embodiments can have commissure attachment portions that are configured to support the commissures of the leaflets at locations spaced radially inwardly toward the longitudinal flow axis of the prosthetic valve relative to the frame portions circumscribing the moveable portions of the leaflets. When the leaflets open under pressure of blood flowing through the prosthetic valve, the moveable portions of the (Continued)

leaflets are retained at positions spaced inwardly from the inner surface of the frame to protect against abrasion of the leaflets.

20 Claims, 15 Drawing Sheets

Related U.S. Application Data

(60) Provisional application No. 61/569,022, filed on Dec. 9, 2011.

(52) U.S. Cl.
CPC .... *A61F 2/2433* (2013.01); *A61F 2220/0075* (2013.01); *A61F 2230/0013* (2013.01); *A61F 2230/0054* (2013.01); *A61F 2250/0036* (2013.01); *A61F 2250/0039* (2013.01)

(58) Field of Classification Search
USPC .............................................. 623/2.11–2.19
See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,192,020 A * | 3/1980 | Davis .................. A61F 2/06 623/2.13 |
| 4,222,126 A | 9/1980 | Boretos et al. |
| 4,265,694 A | 5/1981 | Boretos et al. |
| 4,291,420 A * | 9/1981 | Reul .................. A61F 2/2412 137/846 |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 1,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,350,277 B1 | 2/2002 | Kocur |
| 6,371,983 B1 * | 4/2002 | Lane .................... A61F 2/2409 623/2.14 |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely et al. |
| 6,582,462 B1 | 6/2003 | Andersen et al. |
| 6,605,112 B1 | 8/2003 | Moll |
| 6,652,578 B2 | 11/2003 | Bailey et al. |

(56) References Cited

U.S. PATENT DOCUMENTS

| | | | |
|---|---|---|---|
| 6,730,118 B2 | 5/2004 | Spenser et al. | |
| 6,733,525 B2 | 5/2004 | Yang et al. | |
| 6,767,362 B2 | 7/2004 | Schreck | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 7,018,404 B2 * | 3/2006 | Holmberg | A61F 2/06 623/1.26 |
| 7,018,406 B2 | 3/2006 | Seguin et al. | |
| 7,018,408 B2 | 3/2006 | Bailey et al. | |
| 7,276,078 B2 | 10/2007 | Spenser et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,579,381 B2 | 8/2009 | Dove | |
| 7,585,321 B2 | 9/2009 | Cribier | |
| 7,618,446 B2 | 11/2009 | Andersen et al. | |
| 7,655,034 B2 | 2/2010 | Mitchell et al. | |
| 7,785,366 B2 | 8/2010 | Maurer et al. | |
| 7,959,672 B2 | 6/2011 | Salahieh et al. | |
| 7,993,394 B2 * | 8/2011 | Hariton | A61F 2/2412 623/2.17 |
| 8,007,992 B2 | 8/2011 | Tian et al. | |
| 8,029,556 B2 | 10/2011 | Rowe | |
| 8,167,932 B2 | 5/2012 | Bourang | |
| 8,449,606 B2 | 5/2013 | Eliasen et al. | |
| 8,808,366 B2 * | 8/2014 | Braido | A61F 2/2418 623/1.26 |
| 8,932,343 B2 * | 1/2015 | Alkhatib | A61F 2/2418 623/1.15 |
| 9,168,131 B2 * | 10/2015 | Yohanan | A61F 2/2418 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0114924 A1 * | 6/2003 | Moe | A61F 2/2412 623/2.12 |
| 2003/0158597 A1 | 8/2003 | Quiachon et al. | |
| 2003/0212454 A1 | 11/2003 | Scott et al. | |
| 2004/0039436 A1 | 2/2004 | Spenser et al. | |
| 2004/0133263 A1 | 7/2004 | Dusbabek et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0096736 A1 | 5/2005 | Osse et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2005/0288766 A1 | 12/2005 | Plain et al. | |
| 2006/0025857 A1 | 2/2006 | Bergheim et al. | |
| 2006/0058872 A1 | 3/2006 | Salahieh et al. | |
| 2006/0149350 A1 | 7/2006 | Patel et al. | |
| 2006/0229719 A1 | 10/2006 | Marquez et al. | |
| 2006/0259137 A1 | 11/2006 | Artof et al. | |
| 2007/0005131 A1 | 1/2007 | Taylor | |
| 2007/0005231 A1 | 1/2007 | Seguchi | |
| 2007/0010877 A1 | 1/2007 | Salahieh et al. | |
| 2007/0112422 A1 | 5/2007 | Dehdashtian | |
| 2007/0203503 A1 | 8/2007 | Salahieh et al. | |
| 2007/0203575 A1 | 8/2007 | Forster et al. | |
| 2007/0265700 A1 | 11/2007 | Eliasen et al. | |
| 2008/0065011 A1 | 3/2008 | Marchand et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0161911 A1 | 7/2008 | Revuelta et al. | |
| 2008/0195199 A1 * | 8/2008 | Kheradvar | A61F 2/2418 623/2.11 |
| 2009/0157175 A1 | 6/2009 | Benichou | |
| 2009/0164005 A1 | 6/2009 | Dove et al. | |
| 2009/0171456 A1 | 7/2009 | Kveen et al. | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0168839 A1 | 7/2010 | Braido et al. | |
| 2010/0185277 A1 * | 7/2010 | Braido | A61F 2/2412 623/2.18 |
| 2010/0198347 A1 | 8/2010 | Zakay et al. | |
| 2010/0204781 A1 | 8/2010 | Alkhatib | |
| 2010/0249894 A1 | 9/2010 | Oba et al. | |
| 2010/0268332 A1 | 10/2010 | Tuval et al. | |
| 2011/0015729 A1 | 1/2011 | Jimenez et al. | |
| 2011/0224780 A1 | 9/2011 | Tabor et al. | |
| 2012/0123529 A1 | 5/2012 | Levi et al. | |
| 2012/0179244 A1 * | 7/2012 | Schankereli | A61F 2/2418 623/2.11 |
| 2013/0018458 A1 * | 1/2013 | Yohanan | A61F 2/2418 623/2.18 |
| 2013/0023985 A1 | 1/2013 | Khairkhahan et al. | |
| 2013/0096674 A1 * | 4/2013 | Iobbi | A61F 2/2418 623/2.19 |
| 2013/0166024 A1 * | 6/2013 | Drews | A61F 2/2409 623/2.18 |
| 2013/0317598 A1 | 11/2013 | Rowe et al. | |
| 2014/0222142 A1 * | 8/2014 | Kovalsky | A61F 2/2418 623/2.17 |
| 2014/0303723 A1 * | 10/2014 | Alkhatib | A61F 2/2418 623/2.17 |
| 2014/0343671 A1 * | 11/2014 | Yohanan | A61F 2/2418 623/2.18 |
| 2015/0265401 A1 * | 9/2015 | Braido | A61F 2/2409 623/2.17 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 A2 | 6/2007 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 91/17720 A1 | 11/1991 |
| WO | 92/17118 A1 | 10/1992 |
| WO | 9301768 A1 | 2/1993 |
| WO | 97/24080 A1 | 7/1997 |
| WO | 98/29057 A1 | 7/1998 |
| WO | 99/33414 A1 | 7/1999 |
| WO | 9940964 A1 | 8/1999 |
| WO | 9947075 A1 | 9/1999 |
| WO | 00/18333 A1 | 4/2000 |
| WO | 00/41652 A1 | 7/2000 |
| WO | 00/47139 A1 | 8/2000 |
| WO | 01/35878 A2 | 5/2001 |
| WO | 01/49213 A2 | 7/2001 |
| WO | 01/62189 A1 | 8/2001 |
| WO | 0154624 A1 | 8/2001 |
| WO | 0154625 A1 | 8/2001 |
| WO | 01/64137 A1 | 9/2001 |
| WO | 01/76510 A2 | 10/2001 |

(56) References Cited

FOREIGN PATENT DOCUMENTS

| WO | 02/22054 A1 | 3/2002 |
|---|---|---|
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03047468 A1 | 6/2003 |
| WO | 2005034812 A1 | 4/2005 |
| WO | 2005/087140 A1 | 9/2005 |
| WO | 2005084595 A1 | 9/2005 |
| WO | 2005102015 A2 | 11/2005 |
| WO | 2006/014233 A2 | 2/2006 |
| WO | 2006/034008 A2 | 3/2006 |
| WO | 2006111391 A1 | 10/2006 |
| WO | 2006/138173 A2 | 12/2006 |
| WO | 2007047488 A2 | 4/2007 |
| WO | 2007067942 A1 | 6/2007 |
| WO | 2007097983 A2 | 8/2007 |
| WO | 2008/005405 A2 | 1/2008 |
| WO | 2008/035337 A2 | 3/2008 |
| WO | 2008091515 A2 | 7/2008 |
| WO | 2008/147964 A1 | 12/2008 |
| WO | 2008/150529 A1 | 12/2008 |
| WO | 2009033469 A1 | 3/2009 |
| WO | 2010121076 A2 | 10/2010 |

OTHER PUBLICATIONS

Bailey, S. "Percutaneous Expandable Prosthetic Valves," Textbook of Interventional Cardiology vol. 2, 2nd Ed. pp. 1268-1276. 1994.
H.R. Andersen "History of Percutaneous Aortic Valve Prosthesis," Herz No. 34. pp. 343-346. 2009.
H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Uchida, "Modifications of Gianturco Expandable Wire Stents," American Journal of Roentgenology, vol. 150. pp. 1185-1187. 1986.
Wheatley, "Valve Prostheses," Operative Surgery, 4th ed. pp. 415-424. 1986.

* cited by examiner

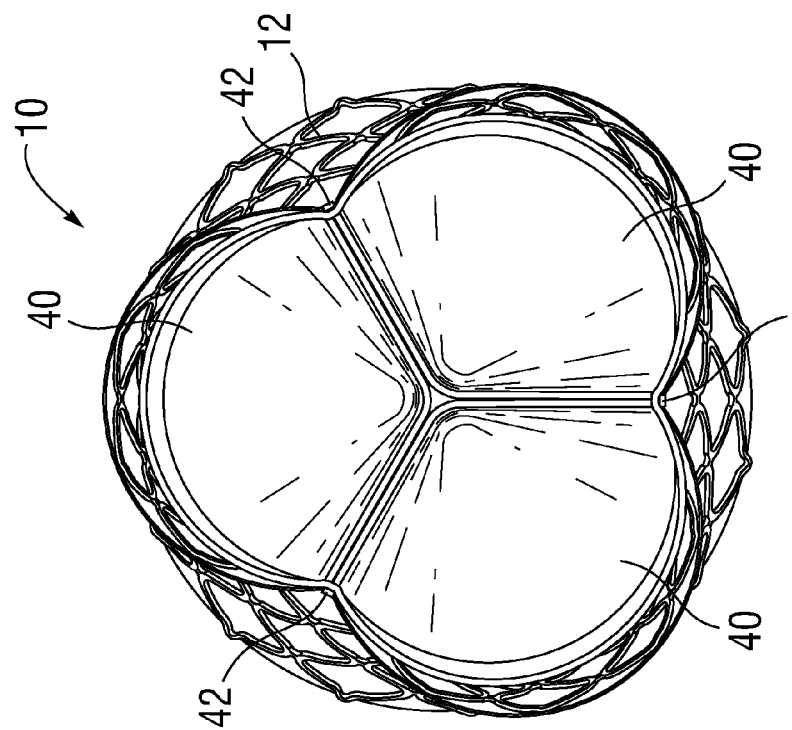
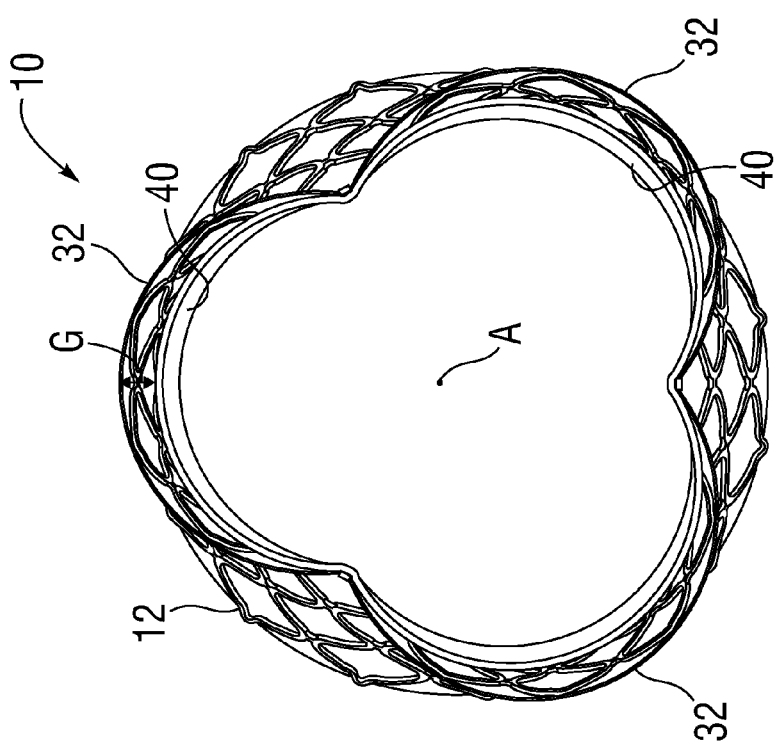
FIG. 3
FIG. 2

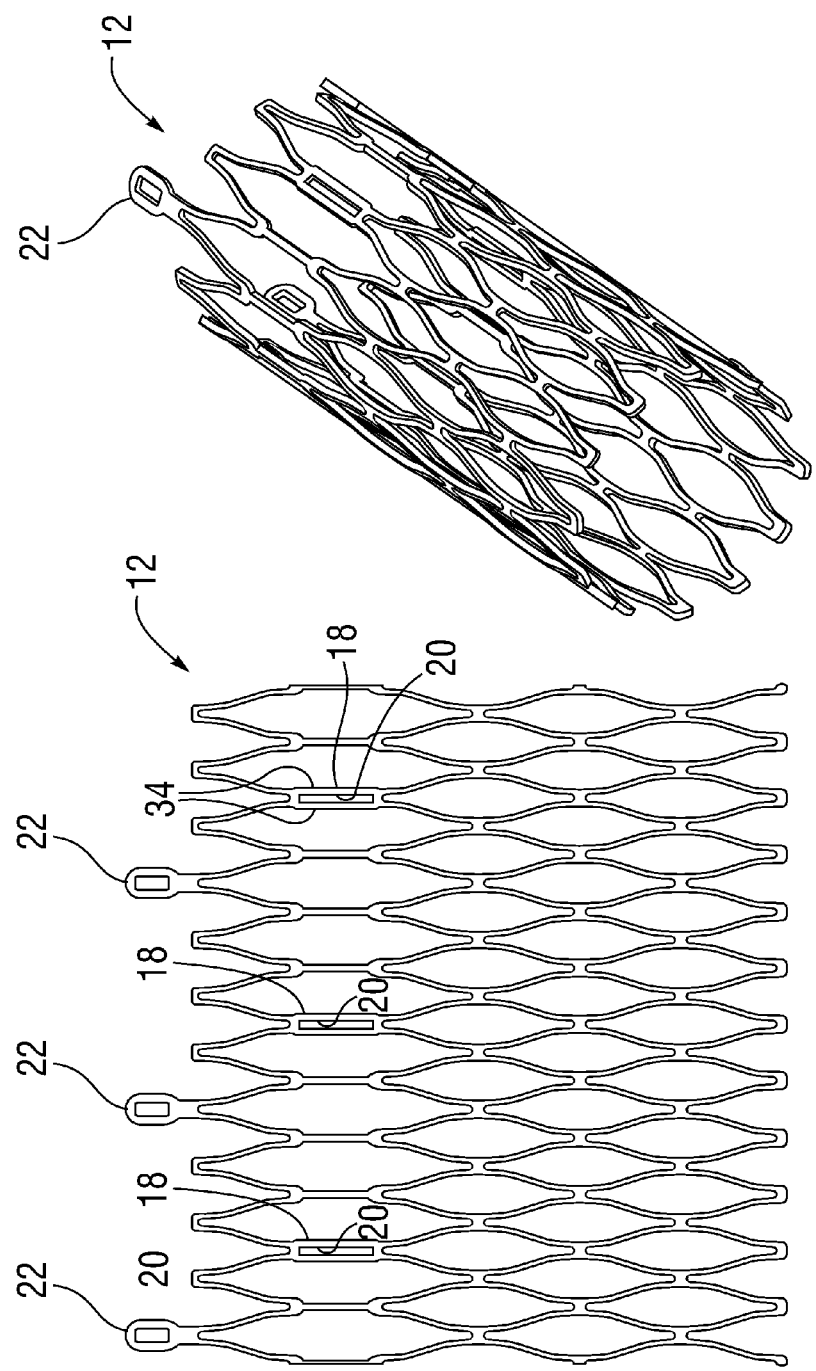

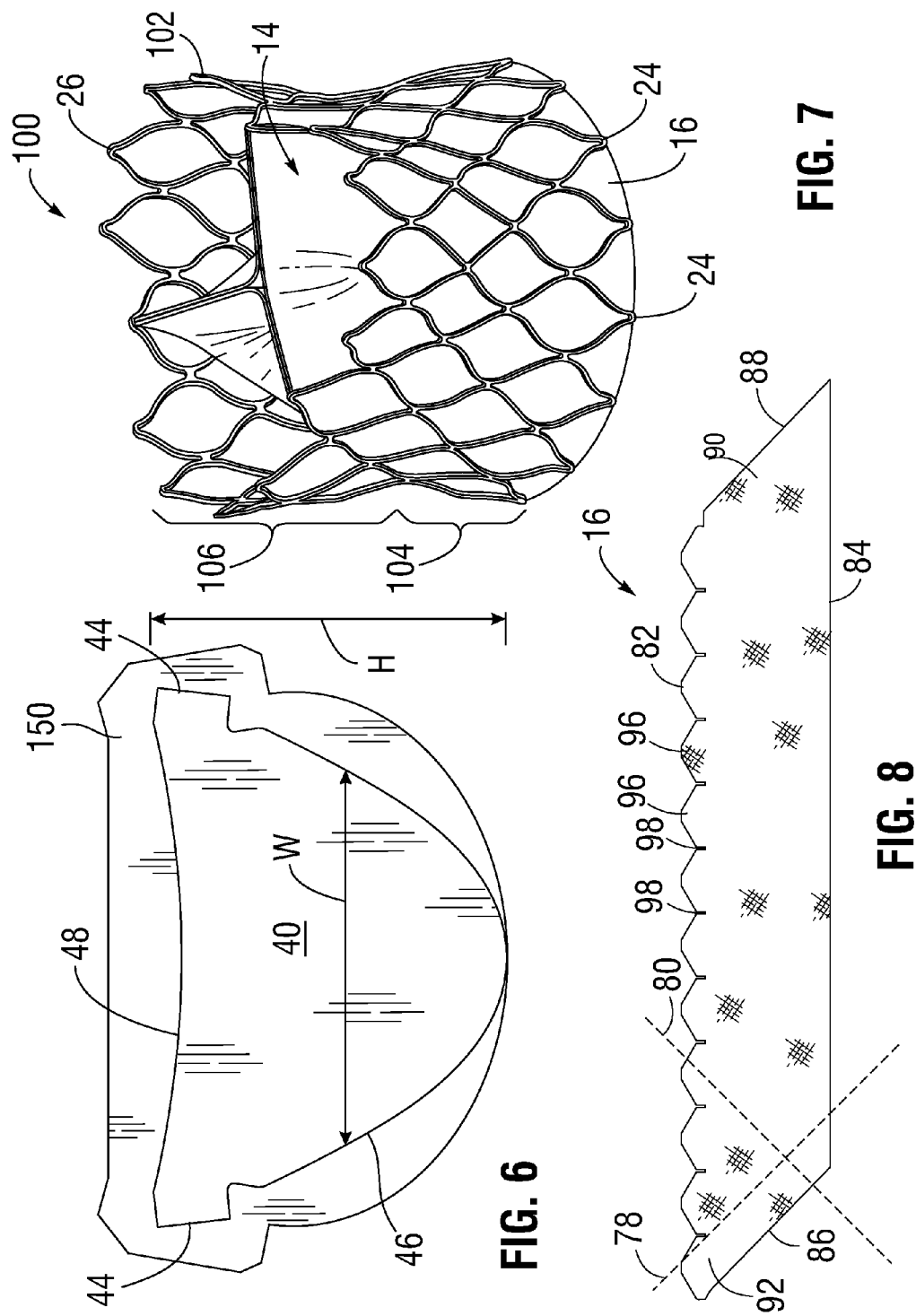

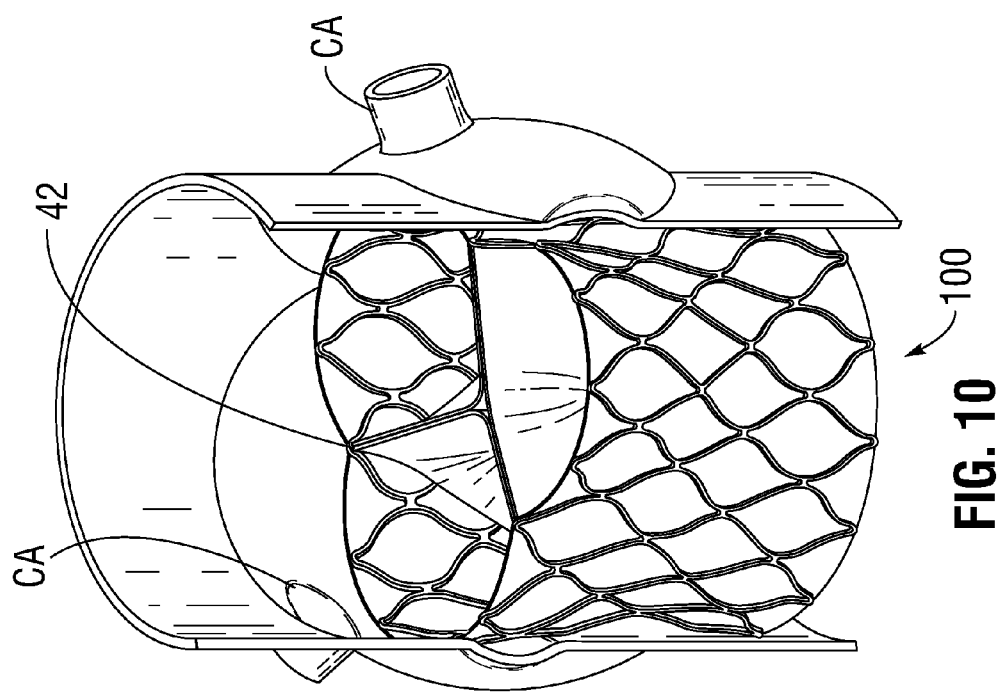
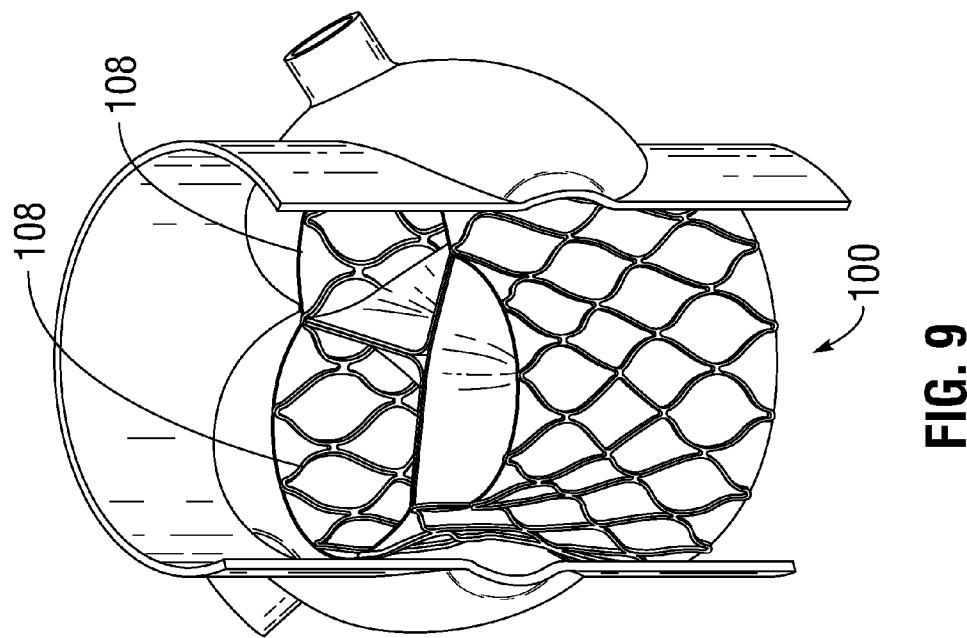
FIG. 10
FIG. 9

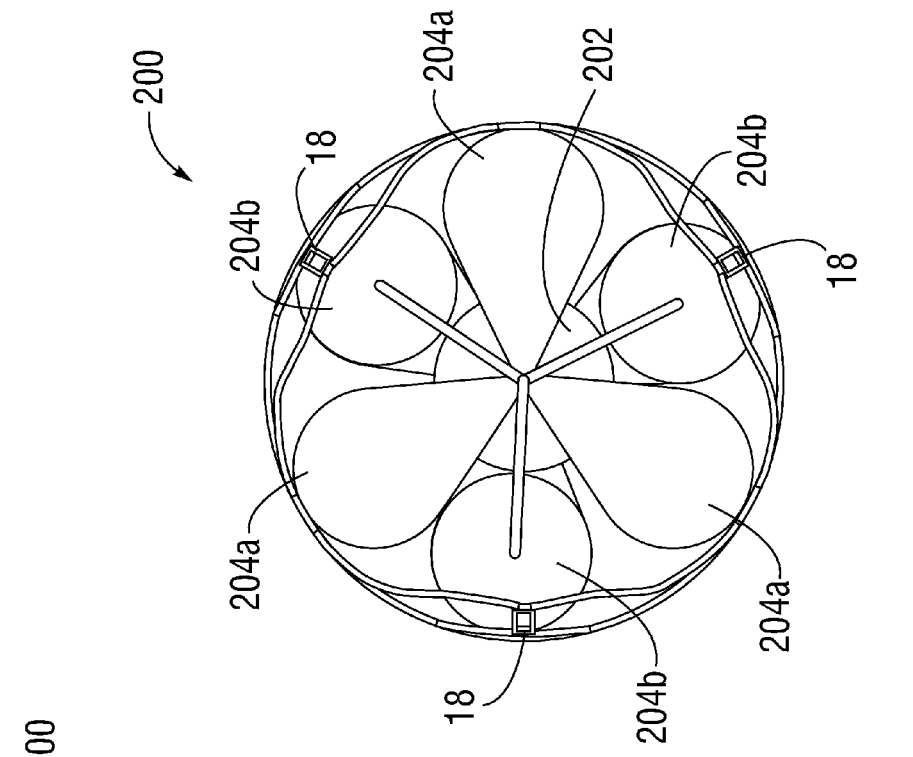
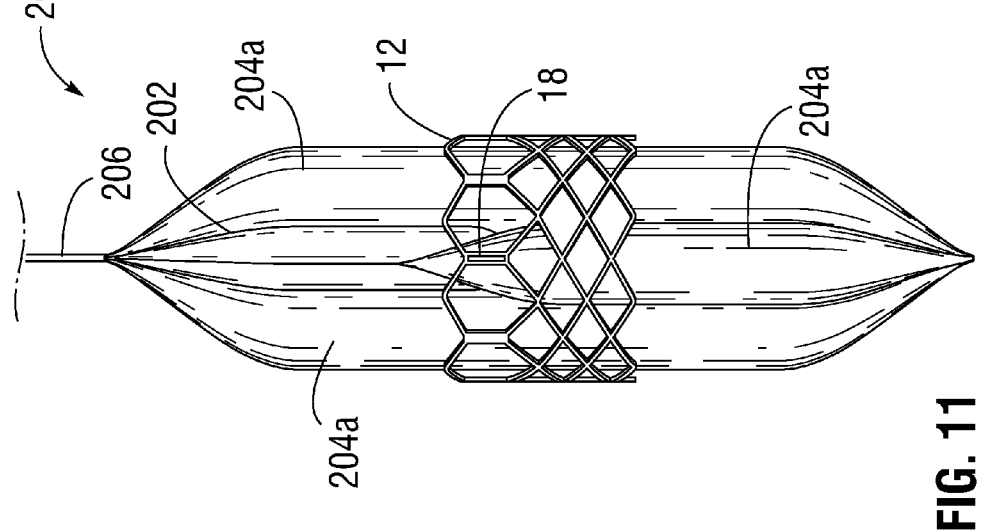

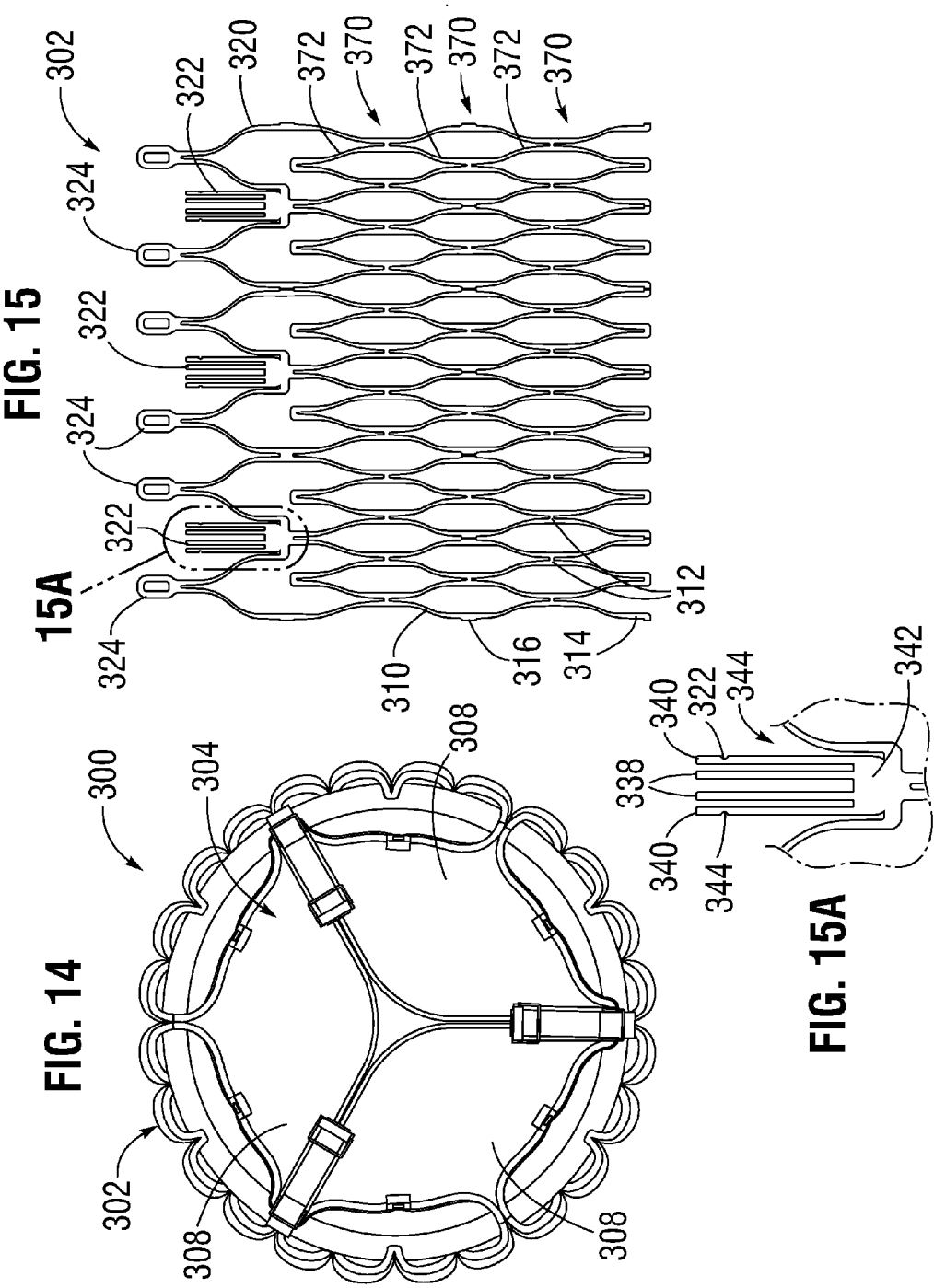

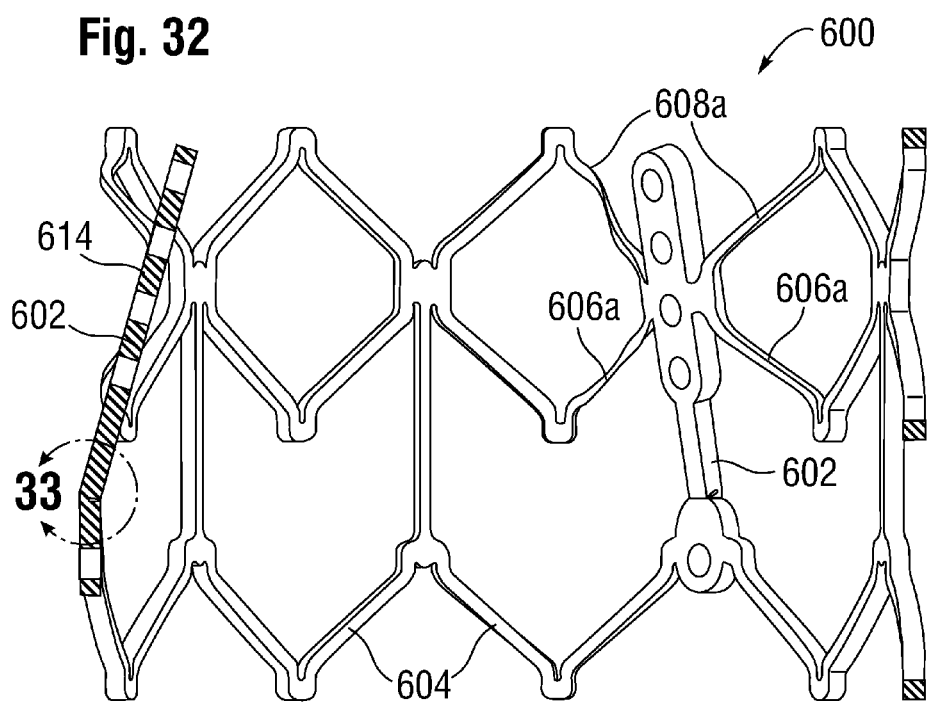
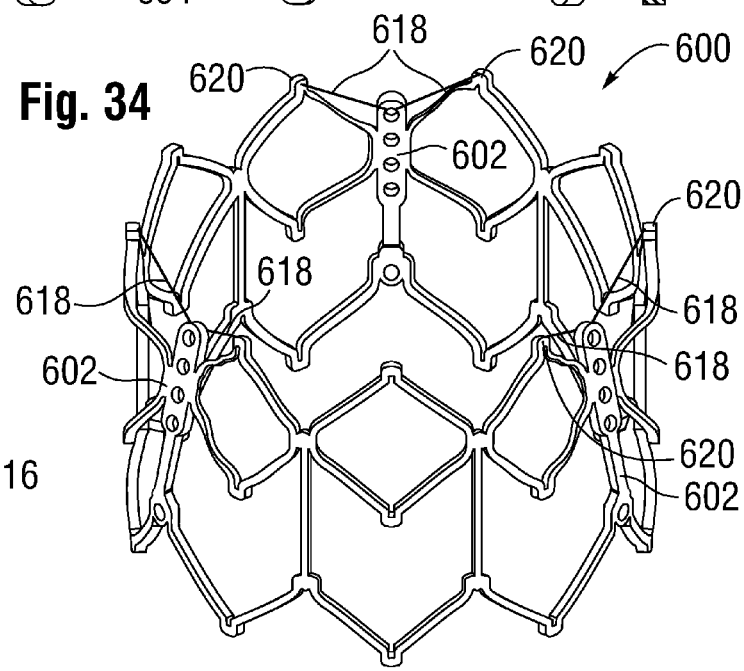

PROSTHETIC HEART VALVE HAVING IMPROVED COMMISSURE SUPPORTS

CROSS REFERENCE TO RELATED APPLICATION

The present application is a continuation of U.S. Non-Provisional application Ser. No. 13/708,598, filed Dec. 7, 2012, which claims the benefit of U.S. Provisional Application No. 61/569,022, filed Dec. 9, 2011, both of which are incorporated herein by reference.

FIELD

The present disclosure concerns embodiments of a prosthetic heart valve, and delivery systems for implanting prosthetic heart valves.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged native valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the native valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter prosthetic heart valves that can be percutaneously introduced in a compressed state on a catheter and expanded in the desired position by balloon inflation or by utilization of a self-expanding frame or stent.

An important design parameter of a transcatheter prosthetic heart valve is the diameter of the folded or crimped profile. The diameter of the crimped profile is important because it directly influences the physician's ability to advance the transcatheter prosthetic heart valve through the femoral artery or vein. More particularly, a smaller profile allows for treatment of a wider population of patients, with enhanced safety.

SUMMARY

The present disclosure is directed to embodiments of catheter-based prosthetic heart valves. A prosthetic heart valve according to the present disclosure comprises a radially collapsible and expandable annular frame and a leaflet structure comprising a plurality of leaflets mounted within the frame. The frame in particular embodiments can have commissure attachment portions that are configured to support the commissures of the leaflets at locations spaced radially inwardly toward the longitudinal flow axis of the prosthetic valve relative to the frame portions circumscribing the moveable portions of the leaflets. When the leaflets open under pressure of blood flowing through the prosthetic valve, the moveable portions of the leaflets are retained at positions spaced inwardly from the inner surface of the frame to protect against abrasion of the leaflets.

In one representative embodiment, a prosthetic valve comprises a radially collapsible and expandable annular frame. The frame has a plurality of angularly spaced commissure attachment portions and a plurality of lobed portions extending between the commissure attachment portions. The frame also has an inlet end and an outlet end. A leaflet structure comprises a plurality of leaflets, each leaflet comprising opposing side portions and an upper edge extending between the side portions. Each side portion is secured to an adjacent side portion of another leaflet to form commissures of the leaflet structure, each commissure being attached to one of the commissure attachment portions of the frame. The leaflets are configured to move between an open position to allow blood to flow through the prosthetic valve from the inlet end to the outlet end and a closed position to inhibit the flow of blood through the prosthetic valve from the outlet end to the inlet end, wherein the upper edges of the leaflets are spaced radially inwardly of the lobed portion of the frame when the leaflets are in the open position.

In another representative embodiment, a prosthetic valve comprises a radially collapsible and expandable annular frame. The frame comprises an inlet portion and an outlet portion, the outlet portion comprising a plurality of angularly spaced, cantilevered commissure attachment posts extending radially inwardly toward a longitudinal flow axis of the prosthetic valve. A leaflet structure comprises a plurality of leaflets, each leaflet comprising opposing side portions, a scalloped upper edge extending between the side portions, and a scalloped lower edge extending between the side portions. Each side portion is secured to an adjacent side portion of another leaflet to form commissures of the leaflet structure, each commissure being attached to one of the commissure attachment posts. The leaflets are configured to move between an open position to allow blood to flow through the prosthetic valve from the inlet portion to the outlet portion and a closed position to inhibit the flow of blood through the prosthetic valve from the outlet portion to the inlet portion, wherein the upper edges of the leaflets are spaced radially inwardly of the frame when the leaflets are in the open position such that a gap is formed between the upper edge of each leaflet and the frame.

In another representative embodiment, a prosthetic valve comprises a radially collapsible and expandable annular frame. The frame has a plurality of angularly spaced commissure attachment posts, each commissure attachment post comprising at least two cantilevered struts spaced apart from each other to define a leaflet-receiving gap. A leaflet structure comprises a plurality of leaflets, each leaflet comprising opposing side portions and an upper edge extending between the side portions. Each side portion is secured to an adjacent side portion of another leaflet to form commissures of the leaflet structure. Each commissure extends through the leaflet-receiving gap of a respective commissure attachment post, and the struts of the commissure attachment post are compressed toward each to clamp the commissure between the struts.

In another representative embodiment, a prosthetic valve comprises a radially collapsible and expandable annular frame that is plastically expandable. The frame comprises a plurality of angularly spaced commissure attachment posts. A leaflet structure comprises a plurality of leaflets, each leaflet comprising opposing side portions, wherein each side portion is secured to an adjacent side portion of another leaflet to form commissures of the leaflet structure, each commissure being attached to one of the commissure attachment posts. The commissure attachment posts are configured to deflect radially inwardly toward a longitudinal flow axis of the prosthetic valve when first subjected to closing forces of the leaflets immediately following implantation of the prosthetic valve and then remain in the deflected position during subsequent closing and opening cycles of the prosthetic valve.

The foregoing and other objects, features, and advantages of the invention will become more apparent from the following detailed description, which proceeds with reference to the accompanying figures.

BRIEF DESCRIPTION OF THE DRAWINGS

FIG. 2 is a top plan view of the prosthetic heart valve of FIG. 1, showing the leaflets in the open position.

FIG. 3 is a top plan view of the prosthetic heart valve of FIG. 1, showing the leaflets in the closed position.

FIG. 4 is a flattened view of the frame of the prosthetic heart valve of FIG. 1, as laser cut from a tubular member.

FIG. 5 is a perspective view of the frame of FIG. 4, as laser cut from a tubular member.

FIG. 6 shows a leaflet of the prosthetic heart valve of FIG. 1, shown on top of a known leaflet for purposes of comparison.

FIG. 7 is a perspective view of a prosthetic heart valve, according to another embodiment.

FIG. 8 shows a flattened view of a skirt for a prosthetic heart valve, according to one embodiment.

FIGS. 9 and 10 show two positions for implanting a prosthetic heart valve in the aortic annulus.

FIG. 11 is a side view of a balloon assembly of a delivery apparatus, according to one embodiment, that can be used for implanting a prosthetic heart valve.

FIG. 12 is a top plan view of the balloon assembly of FIG. 11.

FIG. 14 is a top plan view of the prosthetic valve shown in FIG. 13, showing the leaflets in the closed position.

FIG. 15 is a flattened view of the frame of the prosthetic valve shown in FIG. 13.

FIG. 15A is an enlarged view of a portion of the frame shown in FIG. 15.

FIG. 32 is a cross-sectional view of the frame of FIG. 31.

FIG. 33 is an enlarged view of a weakened portion of the commissure post of the frame shown in FIG. 32.

FIG. 34 is a perspective view of an alternative embodiment of the frame shown in FIG. 29.

DETAILED DESCRIPTION

The present disclosure is directed to embodiments of catheter-based prosthetic heart valves. Several exemplary embodiments of prosthetic heart valves are disclosed herein and shown in the attached figures. These embodiments should not be construed as limiting in any way. Instead, the present disclosure is directed toward all novel and nonobvious features and aspects of the various disclosed embodiments, alone and in various combinations and sub-combinations with one another.

Figure 1:
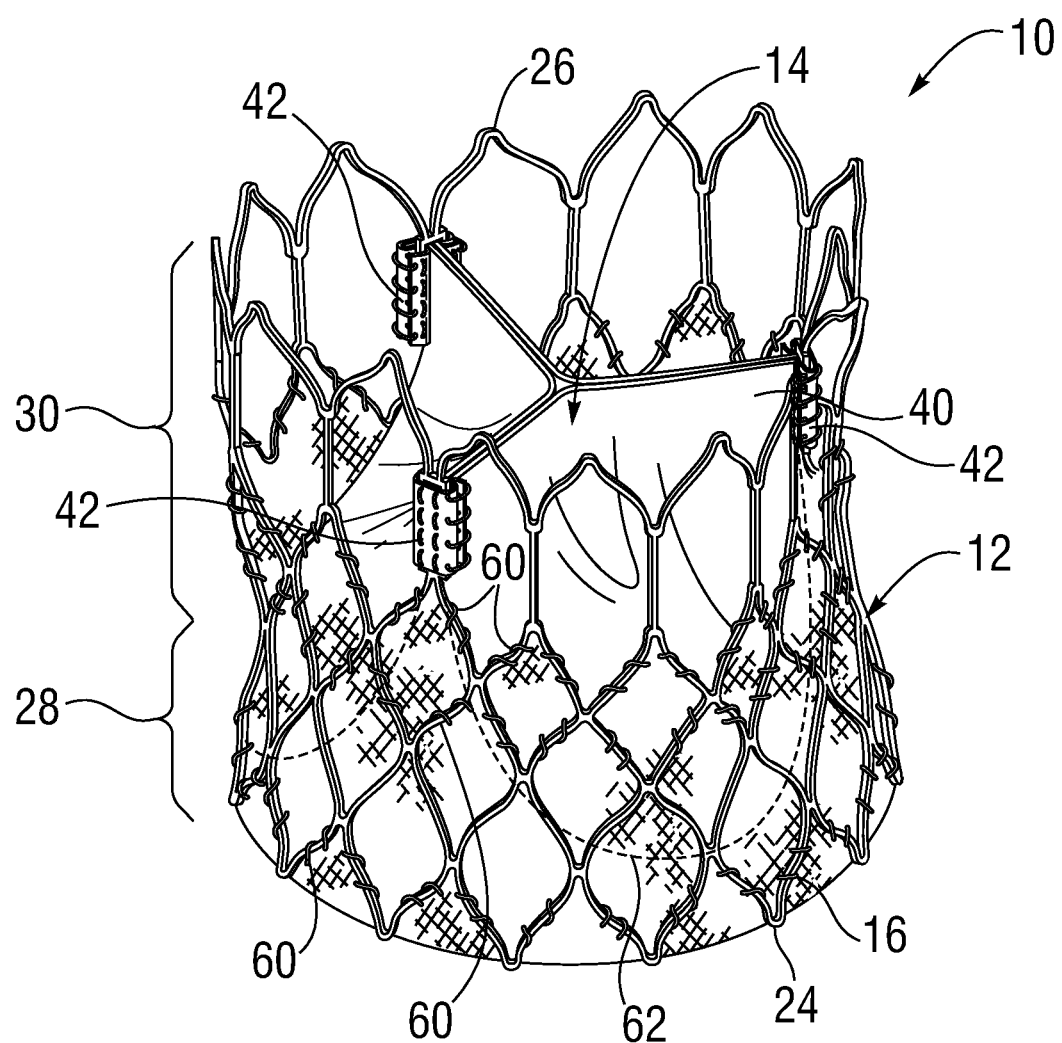
FIG. 1 is a perspective view of a prosthetic heart valve, according to one embodiment.

FIG. 1 is a perspective view of a prosthetic heart valve 10, according to one embodiment. The illustrated prosthetic valve is adapted to be implanted in the native aortic annulus, although in other embodiments it can be adapted to be implanted in the other native annuluses of the heart. The prosthetic valve 10 can have three main components: a stent, or frame, 12, a valvular structure 14, and an inner skirt 16. The prosthetic valve 10 is configured to be radially compressed to a crimped state for delivery into the body of a patient and radially expandable from the crimped state to an expanded state once positioned at the desired implantation location within the body.

The valvular structure 14 can comprise three leaflets 40, collectively forming a leaflet structure, which can be arranged to collapse in a tricuspid arrangement, as best shown in FIG. 3. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

FIG. 4 shows a flattened view of the bare frame 12 and FIG. 5 shows a perspective view of the bare frame as laser cut from a tubular member, prior to any shape forming. The frame 12 can be formed with a plurality of circumferentially spaced commissure supports 18 (three in the illustrated embodiment), each of which comprises two axial struts 34 defining a respective slot, or commissure window, 20 therebetween that is adapted to mount the commissures of the valvular structure 14 to the frame, as described in greater detail below. The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the prosthetic valve 10) can be crimped to a radially compressed state on a delivery catheter and then expanded inside a patient by an inflatable balloon or equivalent expansion mechanism. When constructed of a self-expandable material, the frame 12 (and thus the prosthetic valve 10) can be crimped to a radially compressed state and restrained in the compressed state by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

The frame 12 can also include a plurality of axially extending posts 22 extending from the outflow end of the frame. The posts 22 are used to form a releasable connection between the prosthetic valve 10 and corresponding components at the distal end of a delivery catheter to retain the prosthetic valve at the end of the delivery catheter until the prosthetic valve is properly positioned at its target deployment location within the body. The posts 22 typically are used when the frame is a self-expanding frame since there is no balloon to retain the prosthetic valve in place during deployment. If the frame is a plastically-expandable frame that is deployed with a balloon or similar expansion device, the posts 22 typically are not provided. Details of a delivery device that is configured to retain a self-expandable prosthetic valve via posts 22 is disclosed in U.S. Patent Application Publication No. 2010/0049313, which is incorporated herein by reference.

Referring to FIG. 1, the frame 12 includes an inflow end 24, an outflow end 26, a lower portion 28 and an upper portion 30. As best shown in FIGS. 2 and 3, the upper portion 30 has a tri-lobed cross-sectional shape in a plane perpendicular to the longitudinal axis A of the prosthetic valve at least when the frame is in it expanded state. The upper portion 30 defines three lobed-shaped portions 32 that mimic the shape of the sinuses of the aortic root. The lower portion 28 of the frame desirably has a generally conical or flared shape that tapers from the inflow end 24 toward the upper portion 30 to assist in anchoring the prosthetic valve to the native annulus once implanted. In other embodiments, the lower portion 28 of the frame can have an overall cylindrical shape from the inflow end 24 to the lower end of the upper portion 30. If the frame 12 is constructed of a self-expandable material (e.g., Nitinol), then the frame can be shape set to assume the shape shown in FIGS. 1-3 when the frame radially expands to its expanded state. If the frame 12 is constructed of a plastically-expandable material, then a specially designed delivery device can be used to cause the frame to expand to the shape shown in FIGS. 1-3. One such delivery device is shown in FIGS. 9-11 and described below.

The leaflet assembly 14 defines three commissures 42 where the adjacent sides of the leaflets 40 are secured to each other. The commissures 42 desirably are secured to the upper portion 30 of the frame 12 at locations closest to the longitudinal axis A of the prosthetic valve (which correspond to the locations around the frame where the adjacent ends of the lobed portions 32 meet). The frame 12 can be provided with commissure window frame portions 18 at these locations of the frame to facilitate attachment of the commissures 42 to the frame. Each commissure 42 can be formed by securing each leaflet tab 44 (FIG. 6) with an adjacent tab 44 of another leaflet 40. The commissures 42 can be secured to the frame by inserting each pair of leaflet tabs 44 through a respective slot 20 in a frame portion 18, and securing the leaflet tabs 44 to the axial struts 34, such as with sutures. Further details regarding various techniques for securing the commissures to the window frame portions 18 are disclosed in co-pending U.S. application Ser. No. 13/253,689, filed Oct. 5, 2011, which is incorporated herein by reference.

FIG. 6 shows a leaflet 40 superimposed over a known leaflet 150 for the same size prosthetic valve. As shown, the leaflet 40 in the illustrated embodiment includes a substantially V-shaped lower edge extending between the lower edges of the tabs 44 and a gently curved, or scalloped, upper edge 48 extend between the upper edges of the tabs 44. Because the commissures 42 are secured to the frame 12 at locations spaced radially inwardly toward the longitudinal center axis A relative to the radially outermost sections of the lobed portions 32, the width W of the leaflet (measured between opposing side edges at any location along the height H of the leaflet) can be much less than the width of the leaflet 150. Similarly, the opposing sides of the lower edge 46 can have a greater taper (i.e., the width of the lower portion of the leaflet decreases at a greater rate from top to bottom) than the leaflet 150. Consequently, the leaflets 40 are much smaller than typical conventional leaflets for the same size prosthetic valve, and therefore occupy much less space inside the prosthetic valve. As a result, the prosthetic valve 10 can be crimped to a smaller diameter for delivery.

An important design criterion of a prosthetic heart valve is to prevent or minimize contact between the movable portions of the leaflets and the inner surface of the frame. Repeated contact between the movable portions of the leaflets and the metal frame during operation of the prosthetic valve can cause premature wear and eventual failure of the leaflets. To mount a leaflet assembly to a frame having a cylindrical cross section, it is known, for example, to use additional metal struts or bars or additional layers of material to mount the commissures at locations spaced radially inward from the inner surface of the frame, which assists in preventing contact between the leaflets and the frame. Unfortunately, the use of additional components or additional layers of material for the mounting the commissures takes up valuable space inside of the frame and can limit the overall crimping profile of the prosthetic valve.

To address these concerns, the upper portion 30 of the frame 12 is shaped such that the commissure support portions of the frame are spaced radially inwardly toward the center axis A of the prosthetic valve relative to the adjacent sections of the frame, without using any additional components or layers of material inside the frame to offset the commissures from the inner surface of the frame. As noted above, the commissures 42 of the leaflets are supported at locations where the ends of the lobed portions 32 meet or converge. As a result, contact between the leaflets 40 and the inner surface of the lobed portions 32 can be avoided during operation of the prosthetic valve. As best shown in FIG. 2, the upper free edges 48 of the leaflets are spaced inwardly from the lobed portions 32 by a distance G when the leaflets are open under systolic pressure. Advantageously, since the shape of the frame itself supports the commissures 42 radially inward of the frame sections between the commissure supports 18 without additional components inside of the prosthetic valve, the prosthetic valve 10 can be crimped to a smaller diameter for delivery.

Also due to the shape of the frame, during operation of the prosthetic valve, the commissure supports 18 of the frame can flex slightly radially inwardly and outwardly to reduce stress on the commissure attachment points (the locations were the leaflet tabs 44 are sutured to the frame). As noted above, the leaflets 40 can have a scalloped or curved upper edge 48. As a result, the coaptation lines of the leaflets during diastole are lowered, creating a force vector acting downwardly (axially) from the commissures, which reduces stress on the commissure attachment points.

The prosthetic valve 10 desirably is implanted within a native annulus (e.g., the aortic annulus) such that the lower portion 28 of the frame serves as an anchor to retain the prosthetic valve against the native anatomy. Most of the upper portion 30 of the frame is positioned above the native annulus and has sufficient flexibility to attain the desired size and shape when expanded regardless of the shape of the native annulus. For example, in the case of an oval native annulus, the upper portion 30 of the frame can bend or flex relative to the lower portion 28 in order to expand to its desired functional size and shape to ensure proper operation of the prosthetic valve. In the case of a relatively small native annulus, which can prevent full deployment of the lower portion 28, the upper portion can fully expand to its desired functional size and shape to ensure proper operation of the prosthetic valve.

The frame also is less sensitive to under deployment of the upper portion of the frame. Because the commissures of the leaflets are spaced radially inward from the lobed portions, a radial force applied to the upper portion will first compress the lobed portions in the radial direction before the commissures start to move inwardly. That is, the distance between the commissures 42 stays substantially constant as the lobed portions 32 are radially compressed a predetermined amount. In one implementation, the distance between the commissures 42 stays substantially constant when the diameter of the outflow end of the prosthetic valve is reduced by about 2.5 mm. Thus, if the upper portion of the frame is slightly under expanded due to the positioning of the prosthetic valve and/or the shape of the native annulus, the commissures 42 can still achieve their functional size, which promotes optimum leaflet performance and increased durability of the leaflets. Similarly, because leaflet function is not effected by a certain degree of under expansion of the frame, a prosthetic valve of a certain size can be implanted in a greater range of annulus sizes. Thus, the number of prosthetic valve sizes for treating a wide range of patients can be reduced.

The spaces between the skirt 16 and the outer surfaces of the leaflets 40 within the lobed portions 32 of the frame create artificial sinuses that are shaped similar to and mimic the Valsalva sinuses. Thus, when the leaflets close, backflow entering these artificial sinuses create a turbulent flow of blood along the upper surfaces of the leaflets. This turbulence assists in washing the leaflets and the skirt to minimize clot formation.

The commissures 42 can also be secured to a frame that does not have any window frame portions 18. FIG. 7, for example, shows a prosthetic valve 100, according to another embodiment. The prosthetic valve 100 comprises a frame 102, a valvular structure 14 mounted to the frame 102, and a skirt 16. Like the frame 12 described above, the frame 102 has a generally conical or flared lower portion 104 and a tri-lobed shaped upper portion 106 and functions in the manner described above. The frame 102 comprises a mesh like structure defining a plurality of openings or cells formed by the struts of the frame. The frame 102 has a substantially homogeneous or uniform structure in that the size and shape of all of the openings are substantially the same. The leaflets tabs 44 can be sutured to the struts of the frame 102 adjacent the outflow end and the lower edges 46 of the leaflets 40 (not shown in FIG. 7) can be sutured to the skirt 16 with sutures, as described above in connection with prosthetic valve 10. The frame 102 can also include posts 22 (not shown in FIG. 7) for connection to a delivery apparatus.

The main functions of the skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The skirt 16 desirably comprises a tough, tear resistant material such as polyethylene terephthalate (PET), although various other synthetic or natural materials can be used. The thickness of the skirt desirably is less than 6 mil, and desirably less than 4 mil, and even more desirably about 2 mil. In particular embodiments, the skirt 16 can have a variable thickness, for example, the skirt can be thicker at its edges than at its center. In one implementation, the skirt 16 can comprise a PET skirt having a thickness of about 0.07 mm at its edges and about 0.06 mm at its center. The thinner skirt can provide for better crimping performances while still providing good perivalvular sealing.

As shown in FIG. 1, the skirt 16 can be secured to the inside of frame 12 via sutures 60. Valvular structure 14 can be attached to the skirt via one or more thin PET reinforcing strips (not shown) placed along the lower edges 48 of the leaflets, which enable a secure suturing and protects the pericardial tissue of the leaflet structure from tears. Valvular structure 14 can be sandwiched between skirt 16 and the thin PET strips. Sutures can be used to secure the PET strips and the leaflet structure 14 to the skirt 16 along a suture line 62 that tracks the curvature of the bottom edges 48 of the leaflets.

Referring to FIG. 8, in contrast to known fabric skirts, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees relative to the upper and lower edges 82, 84. The skirt 16 can be formed by weaving the fibers at 45 degree angles relative to the upper and lower edges of the fabric. Alternatively, the skirt can be diagonally cut from a vertically woven fabric (where the fibers extend perpendicular to the edges of the material) such that the fibers extend at 45 degree angles relative to the cut upper and lower edges of the skirt. As further shown in FIG. 8, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall shape of the skirt is that of a rhomboid.

The upper edge portion of the skirt 16 can be formed with a plurality of projections 96 that define an undulated shape that generally follows the shape of the row of struts below the commissure portions 18. In this manner, the upper edge of skirt 16 can be tightly secured to the struts with sutures 60. Skirt 16 can also be formed with slits 98 to facilitate attachment of the skirt to the frame. Slits 98 are dimensioned so as to allow an upper edge portion of skirt to be partially wrapped around the struts and reduce stresses in the skirt during the attachment procedure. For example, skirt 16 is placed on the inside of frame 12 and an upper edge portion of the skirt can be wrapped around the upper surfaces of the struts and secured in place with sutures 60. Wrapping the upper edge portion of the skirt around the struts in this manner provides for a stronger and more durable attachment of the skirt to the frame.

Due to the orientation of the fibers relative to the upper and lower edges, the skirt can undergo greater elongation in the axial direction (i.e., in a direction from the upper edge 82 to the lower edge 84). Thus, when the metal frame 12 is crimped, the skirt 16 can elongate in the axial direction along with the frame and therefore provides a more uniform and predictable crimping profile. Each cell of the metal frame in the illustrated embodiment includes at least four angled struts that rotate towards the axial direction (i.e., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET skirt 16 formed from 20-denier yarn, the yarn density can be about 15% to about 30% less than a conventional PET skirt. In some examples, the yarn spacing of the skirt 16 can be from about 155 yarns per inch to about 180 yarns per inch, such about 160 yarns per inch, whereas in a conventional PET skirt the yarn spacing can be from about 217 yarns per inch to about 247 yarns per inch. The oblique edges 86, 88 promote uniform and even distribution of the fabric material along inner circumference of the frame during crimping so as to minimize bunching of the fabric to facilitate uniform crimping to the smallest possible diameter. Additionally, cutting diagonal sutures in a vertical manner may leave loose fringes along the cut edges. The oblique edges 86, 88 help minimize this from occurring.

The prosthetic valves disclosed herein can also include an outer skirt (not shown) secured to the outside of the frame. The outer skirt assists in forming a good seal between the prosthetic valve and the native annulus to avoid perivalvular leaks. An outer skirt is further described in co-pending U.S. application Ser. No. 13/253,689, filed Oct. 5, 2011, which is incorporated herein by reference.

The prosthetic valves disclosed herein can be implanted via known techniques. For example, a prosthetic valve can be implanted in a retrograde approach where the prosthetic valve, mounted in a crimped state at the distal end of a delivery apparatus, is introduced into the body via the femoral artery and advanced through the aortic arch to the heart. A prosthetic valve can also be also be implanted via a transapical approach where the prosthetic valve, mounted in a crimped state at the end of a delivery apparatus, is inserted into the heart via a surgical incision in the chest and the apex of the heart.

FIGS. 9 and 10 show two possible positions for implanting a prosthetic heart valve of the present disclosure within the native aortic valve. FIG. 9 shows a first position in which the lobed portions 108 of prosthetic valve 100 are aligned with the native sinuses in the aortic root to fit the native anatomy. FIG. 10 shows a second position in which the prosthetic valve 100 is rotated 60 degrees from the position shown in FIG. 9. In the position shown in FIG. 10, the commissures 42 of the prosthetic valve are generally aligned with the coronary arteries to maximize the space between the openings of the coronary arteries and the outer surface of the prosthetic valve.

FIGS. 11-12 show a balloon assembly 200 of a delivery apparatus, according to one embodiment, that can be used to expand a prosthetic valve to an expanded shape in which the commissure supports 18 are bent radially inwardly relative to the sections of the frame extending between the commissure supports. The balloon assembly 200 is mounted to the distal end of an elongated shaft 206 of the delivery apparatus. The balloon assembly 200 in the illustrated embodiment includes a center balloon 202 and a plurality of peripheral balloons 204a, 204b surrounding the center balloon. The proximal ends of all of the balloons can be fluidly connected to a central inflation lumen extending through the shaft 206, which allows an inflation fluid to flow into each of the balloons.

The peripheral balloons include a first set of balloons 204a and a second set of relatively shorter balloons 204b that do not extend the entire length of the balloon assembly. Each of the shorter balloons 204b is positioned between two longer balloons 204a. The bare frame 12 (without leaflets or skirt) is shown in FIGS. 11 and 12 for purposes of illustration. When the prosthetic valve 10 is crimped and positioned on the balloon assembly 200 for delivery in a patient, the commissure supports 18 are aligned with the tapered ends of the shorter balloons 204b. Thus, when the balloons are inflated, the portion of the frame 12 below the commissure supports 18 expands to a cylindrical configuration, while the commissure portions 18 do not fully expand and therefore are titled or bent radially inwardly relative to the struts extending between the commissure portions.

Figure 13:
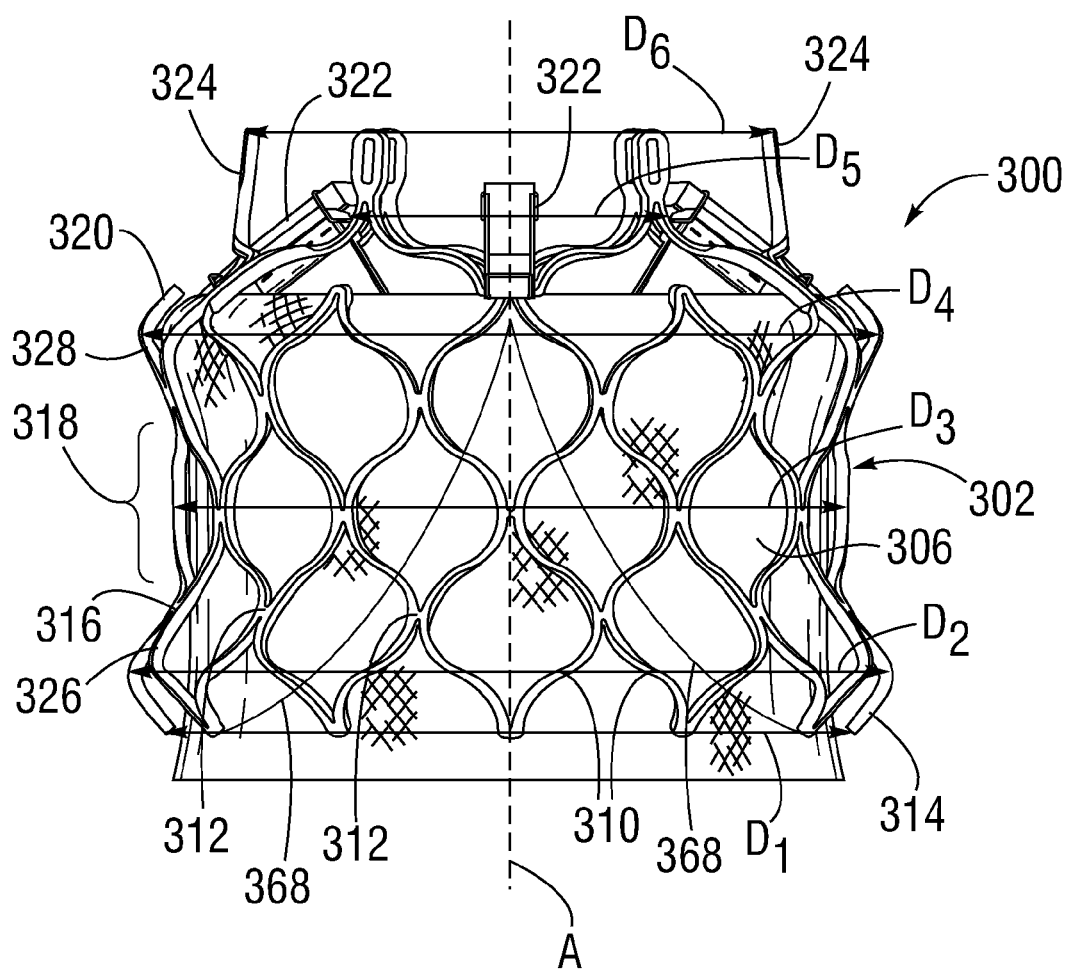
FIG. 13 is a side elevation of a prosthetic heart valve, according to another embodiment.

FIG. 13 is a side elevation view of a prosthetic heart valve 300, according to another embodiment. FIG. 14 is a top plan view of the prosthetic valve 300. The illustrated prosthetic valve is adapted to be implanted in the native aortic annulus, although in other embodiments it can be adapted to be implanted in the other native annuluses of the heart. The prosthetic valve 300 can have three main components: a stent, or frame, 302, a valvular structure 304, and an inner skirt 306. The prosthetic valve 300 is configured to be radially compressed to a crimped state for delivery into the body of a patient and radially expandable from the crimped state to an expanded state once positioned at the desired implantation location within the body.

The valvular structure 304 can comprise three leaflets 308, collectively forming a leaflet structure, which can be arranged to collapse in a tricuspid arrangement, as best shown in FIG. 14. The leaflets 308 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

As shown in FIG. 13, the frame 302 comprises a plurality of longitudinally extending, sinusoidal-shaped or undulating struts 310 connected to each other at nodes 312 so as to define a plurality of open cells arranged in rows along the longitudinal flow axis of the frame. The frame 302 comprises an inflow end portion 314 that increases in diameter from a diameter D1 at an inflow end of the frame to a relatively larger diameter D2 at a distance spaced from the inflow end of the frame. An intermediate portion 316 of the frame defines a "landing zone" for the frame in that the intermediate portion is positioned within the native annulus when the prosthetic valve is deployed. The intermediate portion initially decreases in diameter from diameter D2 to a relatively smaller diameter D3 at about a middle section 318 of the intermediate portion and then increases in diameter to a diameter D4 proximate the outflow end of the frame. The middle section 318 of the intermediate portion can be a cylindrical shape having a relatively constant diameter D3 along the length of the frame between the section that decreases in diameter from diameter D2 to diameter D3 and the section that increases in diameter from D3 to diameter D4. An outflow portion 320 of the frame decreases in diameter from diameter D4 at the outflow end of the intermediate portion to a diameter D5 at an outflow end of the frame. In particular embodiments, D2 is equal to D4, D1 is equal to D3, and D5 is less than D1, D2, D3 and D4.

FIG. 15 shows the frame 302 in a flattened, or unrolled, configuration. As best shown in FIG. 15, the outflow end portion 320 of the frame comprises a plurality of circumferentially spaced, longitudinally extending commissure attachment portions, or posts, 322 interspaced between a plurality of frame retaining arms, or posts, 324. The retaining arms 324 are used to form a releasable connection between the prosthetic valve 300 and corresponding components at the distal end of a delivery catheter to retain the prosthetic valve at the end of the delivery catheter until the prosthetic valve is properly positioned at its target deployment location within the body. The retaining arms 324 typically are used when the frame is a self-expanding frame since there is no balloon to retain the prosthetic valve in place during deployment. If the frame is a plastically-expandable frame that is deployed with a balloon or similar expansion device, the retaining arms typically are not provided. Details of a delivery device that is configured to retain a self-expandable prosthetic valve via retaining arms 324 is disclosed in U.S. Patent Application Publication No. 2010/0049313, which is incorporated herein by reference. In the illustrated embodiment, the frame 302 has six such retaining arms 324, although a greater or fewer number of retaining arms may be used. Also, the frame 302 in the illustrated embodiment has three commissure attachment portions 322 corresponding to the three commissures formed by the leaflets 308. The frame can have a greater or fewer number of commissure attachment portions 322 if there are a greater or fewer number of commissures formed by the leaflets 308.

As shown in FIG. 13, the retaining arms 324 in the illustrated configuration extend generally parallel to the flow axis A of the prosthetic valve, or inwardly at a very small angle (e.g., about 1-2 degrees) with respect to the flow axis A, while the commissure attachment portions 322 extend inwardly at a much sharper angle with respect the flow axis A. In particular embodiments, for example, the commissure attachment portions 322 extend inwardly with respect to the flow axis A at an angle of about 10 degrees to about 60 degrees, and more particularly, at an angle of about 15 degrees to about 45 degrees. The upper free ends of the commissure attachment portions 322 define the outflow diameter D5 of the prosthetic valve. The retaining arms 324 define a diameter D6, which can be greater than the outflow diameter D5.

The shape of the frame 302 as depicted in FIG. 13 has several advantages. The prosthetic valve 300 typically is positioned within the sheath of a delivery apparatus such that the inflow end portion 314 is adjacent the distal opening of the sheath. The tapered inflow end portion 314 can obviate the need for a separate nose cone at the distal end of the delivery apparatus, which typically is used to shield the end of the frame from contacting surrounding tissue during delivery of the prosthetic valve through the patient's vasculature. The tapered inflow end portion 314, which typically is deployed first from the sheath during retrograde delivery to the native aortic valve, can reduce the risk of trauma to native tissue, such as the aortic annulus and the native leaflets, as the prosthetic valve is deployed from the sheath. The tapered inflow end portion also reduces the risk of conduction system obstruction.

The tapered outflow portion 320 of the frame reduces the risk of obstructing the coronary ostia when the prosthetic valve is implanted in the native aortic annulus. When implanted, the outflow portion is spaced inwardly of the aortic root, allowing blood to flow into the coronary arteries. Moreover, the tapered outflow portion can reduce the risk that calcified native leaflets will be pushed against and block the coronary ostia. Also, when deploying, positioning, or retrieving the prosthetic valve and during normal operation of the implanted prosthetic valve, the tapered outflow portion reduces the risk of interaction with the sinotubular junction.

The shape of the intermediate section 316 facilitates positioning of the prosthetic valve by providing a relative large middle section 318 for positioning within the native annulus. The enlarged inflow and outflow sections 326, 328, respectively, of the intermediate section 316 (at D2 and D4) assist in centering the prosthetic valve lengthwise with respect to the native annulus. The enlarged inflow and outflow sections 326, 328 also enhance anchoring of the prosthetic valve by engaging the lower and upper portions of the native valve. Thus, the inflow section 326 can engage the ventricular side of the native aortic valve and inhibit implant migration toward the aorta, while the outflow section 328 can engage the aortic side of the native aortic valve and inhibit implant migration toward the left ventricle. In this manner, the intermediate portion 316 can provide stable fixation for the prosthetic valve even for a non-calcified aortic root. Moreover, contact between the enlarged inflow section 326 and adjacent tissue and between the enlarged outflow section 328 and adjacent tissue can enhance perivalvular sealing between the skirt 306 and the native annulus.

Another advantage of the frame design is that is facilitates re-sheathing and/or repositioning of the prosthetic valve. As noted above, the retaining arms 324 of the frame can be secured to connection devices on the distal end of the delivery apparatus when the prosthetic valve is being implanted in the body. Under ideal circumstances, the prosthetic valve is implanted by deploying the prosthetic valve from the sheath of the delivery apparatus at or near the deployment location, adjusting the position of the prosthetic valve (if necessary) and releasing the connection between the retaining arms 324 and the delivery apparatus. In some cases, it may be necessary or desirable to fully or partially re-sheath the prosthetic valve (retract the prosthetic valve back into the sheath) after it is deployed in order to reposition the prosthetic valve or to remove it completely from the body. Because the commissure attachment portions 322 extend radially inwardly relative to the retaining arms 324, the distal ends of the commissure attachment portions 322 can be retained in a compressed state having a compressed diameter smaller than the inner diameter of the sheath of the delivery apparatus. Thus, even if the prosthetic valve is fully deployed from the delivery sheath, the commissure attachment portions 322 can be retracted back into the sheath, followed by the remaining portion of the prosthetic valve for repositioning the prosthetic valve or withdrawing it from the body.

Figure 16:
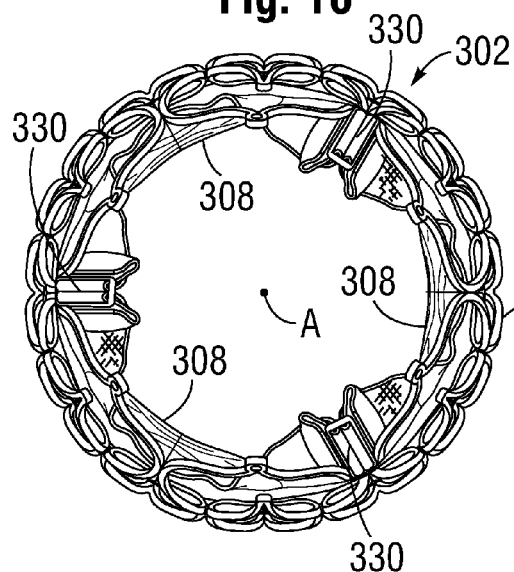
FIG. 16 is a top plan view of the prosthetic valve of FIG. 13, showing the leaflets in the open position.
Figure 17:
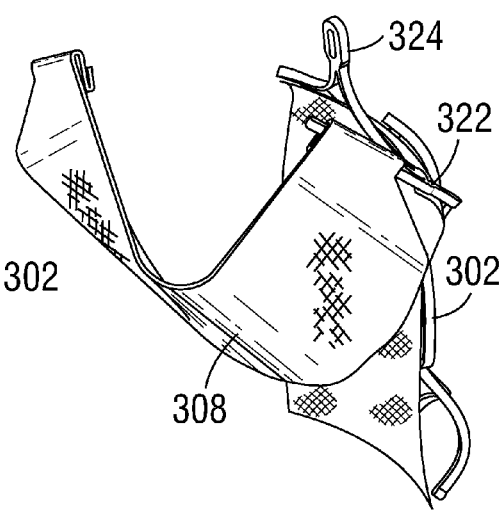
FIG. 17 is a perspective view of a leaflet and a portion of the frame of the prosthetic valve of FIG. 13, showing the commissure of the leaflet supported at angle of about 60 degrees relative to the longitudinal flow axis of the valve.
Figure 18:
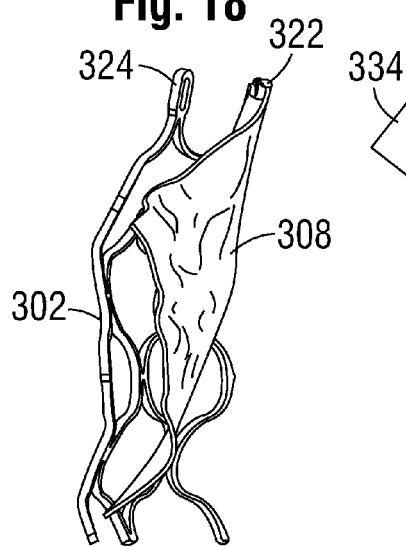
FIG. 18 is a perspective view similar to FIG. 17, showing the commissure of the leaflet supported at an angle of about 15 degrees relative to the longitudinal flow axis of the prosthetic valve.

FIG. 16 is a top plan view of the prosthetic valve 300 with the skirt 306 removed for purposes of illustration. FIG. 16 also shows the leaflets 308 in an open position under systolic pressure, allowing blood to flow through the prosthetic valve. As can be seen, the cantilevered and angled commissure attachment portions 322 support respective commissures 330 of the valvular structure inwardly toward the central flow axis A and away from adjacent portions of the frame 302 to avoid contact between the moveable portions of the leaflets and the frame. The angled commissure attachment portions 322 also reduce the distance between the commissures, enabling a more efficient leaflet design, as further described below. As noted above, the angle of the commissure attachment portions 322 can be varied depending on the particular application. FIG. 17 shows an embodiment where the commissure attachment portions 322 extend inwardly at about a 60-degree angle relative to the retaining arms 324. FIG. 18 shows an embodiment where the commissure attachment portions 322 extend inwardly at about a 15-degree angle relative to the retaining arms 324.

Figure 19:
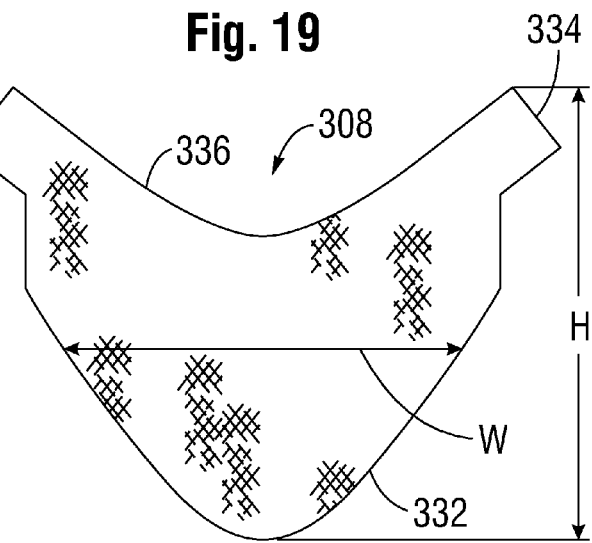
FIG. 19 is a flattened view of a leaflet of the prosthetic valve of FIG. 13.

FIG. 19 shows a leaflet 308 of the valvular structure 304. The leaflet 308 in the illustrated embodiment comprises a substantially V-shaped or scalloped lower edge 332 extending between the lower edges of tabs 334 and a substantially V-shaped or scalloped upper edge 336 extending between the upper edges of the tabs 334. By reducing the distance between the commissures 330, the width W of the leaflet 308 (measured between opposing side edges at any location along the height H of the leaflet) can be minimized and the upper edge 336 can have a relatively pronounced concavity, which reduces the overall size of the leaflet compared to a known leaflet 150 (FIG. 6) for the same size prosthetic valve. The smaller, more efficient leaflet design occupies much less space inside the crimped prosthetic valve and therefore allows the prosthetic valve to be crimped to a smaller diameter for delivery.

Because the commissure attachment portions 322 are cantilevered relative to the frame, they can deflect slightly during operation of the prosthetic valve, which improves valve operation and durability. In particular, when the leaflets 308 close under diastolic pressure, the commissure attachment portions 322 can deflect inwardly to relieve stress and strain on the leaflets (especially the commissure attachment points of the leaflet tabs 334), which improves long term durability of the leaflets. Also, when the leaflets open under systolic pressure (as depicted in FIG. 16), the upper edges 336 of the leaflets are retained at a position spaced from the inner surface of the frame to prevent abrasion and increase leaflet durability. Providing an enlarged diameter D4 (FIG. 13) within the outflow portion 320 of the frame also assists in creating a gap between the inner surface of the frame and the leaflets when the leaflets are in the open position.

The cantilevered commissure attachment portions 322 can also help avoid "pinwheeling" of the leaflets. "Pinwheeling" is a phenomenon characterized by twisting of the upper edges of the leaflets when the leaflets close under diastolic pressure. The twisting motion results in increased flexion and stress on the leaflets, which can adversely effect the durability of the leaflets. The flexible commissure attachment portions 322 can absorb some of the closing forces on the leaflets and allow the leaflets to close more gently under diastolic pressure, thereby preventing or at least minimizing the pinwheeling effect.

The concave upper edges 336 of the leaflets and the cantilevered commissure attachment portions 322 can also help avoid "reverse bending" of the leaflets. "Reverse bending" of leaflets refers to irregular folds or bends that can occur when the leaflets open under systolic pressure. The stresses generated on the leaflet tissue by such bending or folding of the leaflets can lead to fatigue failure of the leaflet. When the leaflets 308 open under systolic pressure, the commissure attachment portions 322 are deflect slightly outwardly away from the flow axis A, taking up or reducing slack along the upper edges 336 of the leaflets. This inhibits the formation of irregular folds or bends in the leaflets, allowing the leaflets mimic the shape of the native aortic leaflets in the open position. The concave upper edges of the leaflets also reduces the amount of slack between the commissures to further ensure the leaflets can be achieve a more natural shape without irregular folds or bends when opened under systolic pressure.

FIG. 15A is an enlarged view of a commissure attachment portion 322. The commissure attachment portion 322 comprises at least two cantilevered struts that are configured to provide a clamping or pinching force against a pair of leaflet tabs 334 to assist in securing the leaflet tabs to the frame. In the illustrated configuration, each attachment portion 322 comprises two cantilevered inner struts 338 and two cantilevered outer struts 340 extending from a common base 342. The two inner struts 338 are spaced apart from each other to define a leaflet-receiving gap therebetween. Similarly, each outer strut 340 is spaced apart from a corresponding adjacent inner strut 338 to define a respective leaflet-receiving gap therebetween. The inner and outer struts 338, 340 are used to secure the commissures 330 of the leaflets. Each outer strut 340 can be formed with a small recess or notch 344 that can be used to retain a suture that extends around the attachment portion 322, as further described below.

Figure 21:
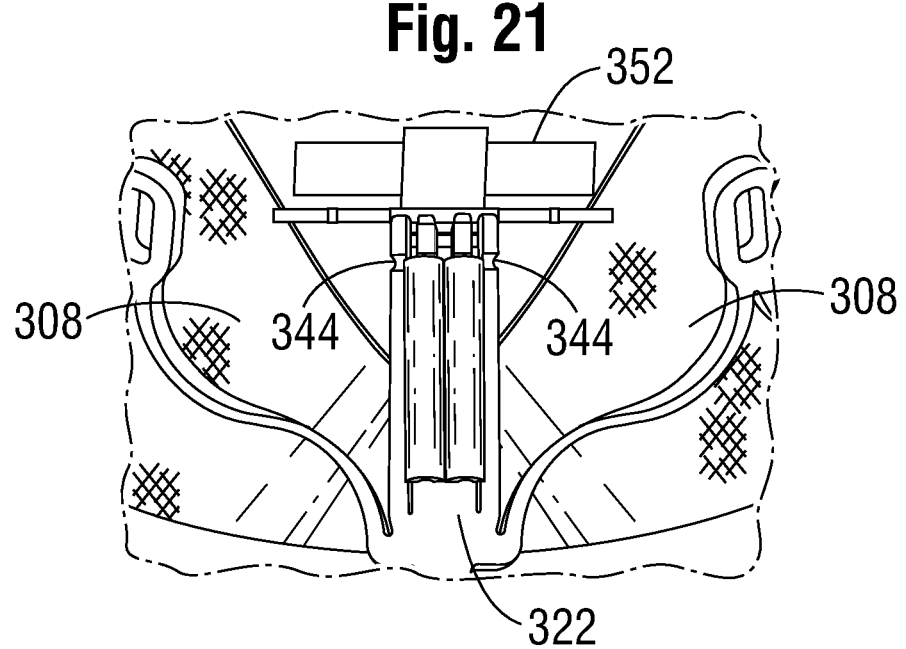
Figure 22:
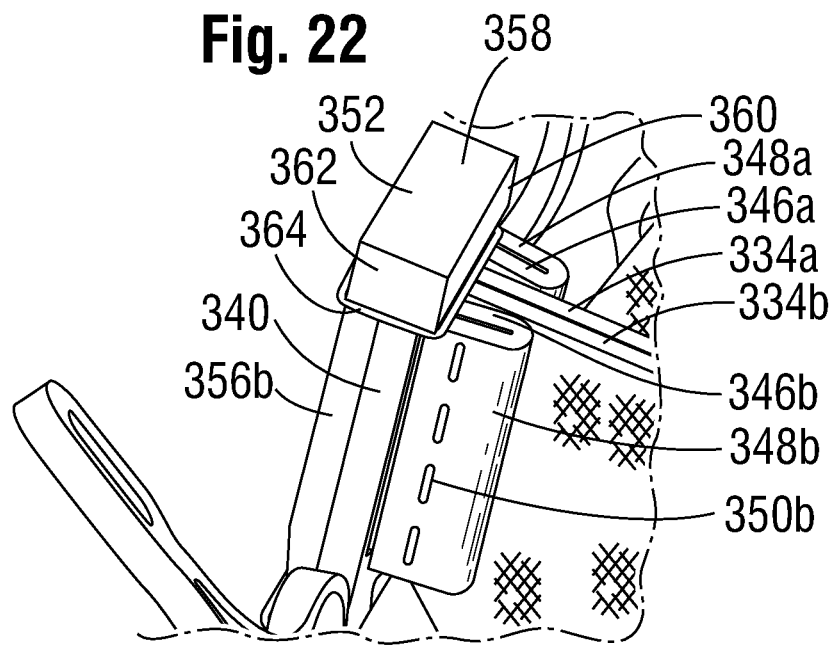
Figure 23:
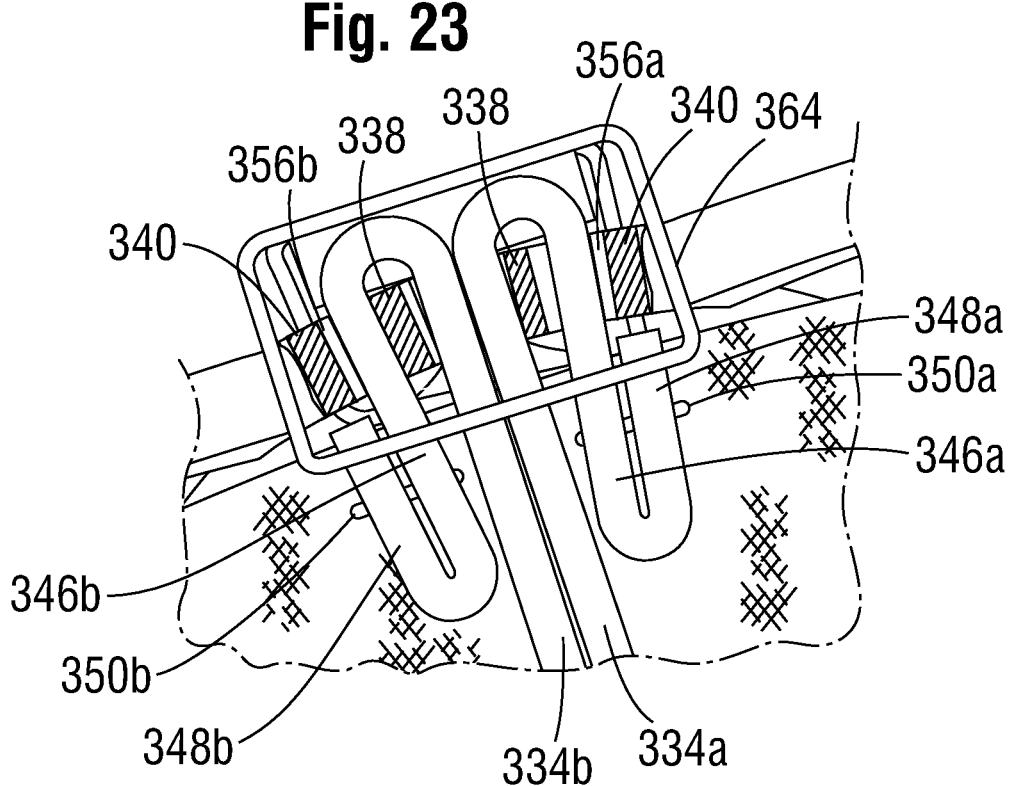

Referring now to FIGS. 20-25, a method for securing the commissures 330 to the commissure attachment portion 322 will now be described. Each commissure attachment portion 322 supports a pair of adjacent tab portions 334 of two leaflets 308 on the inner and outer struts 338, 340. As best shown in FIG. 23, a pair of tab portions 334a and 334b extend through the gap between the inner struts 338. On the radial outer side of the commissure attachment portion, the tab portions 334 are folded away from each other, forming a first fold 346a and a second fold 346b. The first fold 346a extends through a respective gap between an inner strut 338 and an adjacent outer strut 340. The second fold 346b extends through a respective gap between the inner strut 338 and the adjacent outer strut 340. Tab portion 334*a* can then be folded again to form a fold 348*a* that lies against the outside of fold 346*a*. Likewise, tab portion 334*b* can be folded again to form a fold 348*b* that lies against the outside of fold 346*b*. Fold 348*a* can be secured to fold 346*a* by a suture 350*a* that extends along the length of the folds. Likewise, fold 348*b* can be secured to fold 346*b* by a suture 350*b* that extends along the length of the folds.

Each pair of the tab portions 334 can be reinforced with a reinforcement portion 352, which can be cut or otherwise formed from a sheet of strong, flexible material, such as PET. The reinforcement portion 352 reinforces the connection of the leaflet tab portions to the frame and protects the portions of the leaflets on the outside of the frame from contacting the delivery sheath. The reinforcement portions 352 can be three separate pieces of material mounted to the commissure attachment portions 322. Alternatively, the reinforcement portions 352 can be integral upper extensions of the skirt 306 (i.e., the skirt 306 and the reinforcement portions 352 can be a single piece of material).

Figure 20:
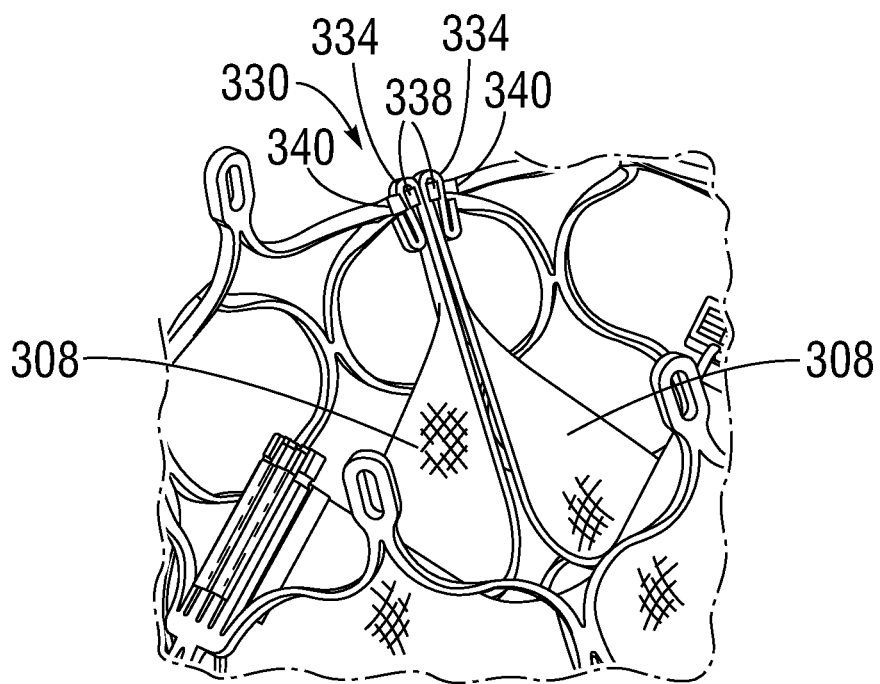
FIGS. 20-25 are various views illustrating the connection of a commissure to the frame of the prosthetic valve of FIG. 13.
Figure 24:
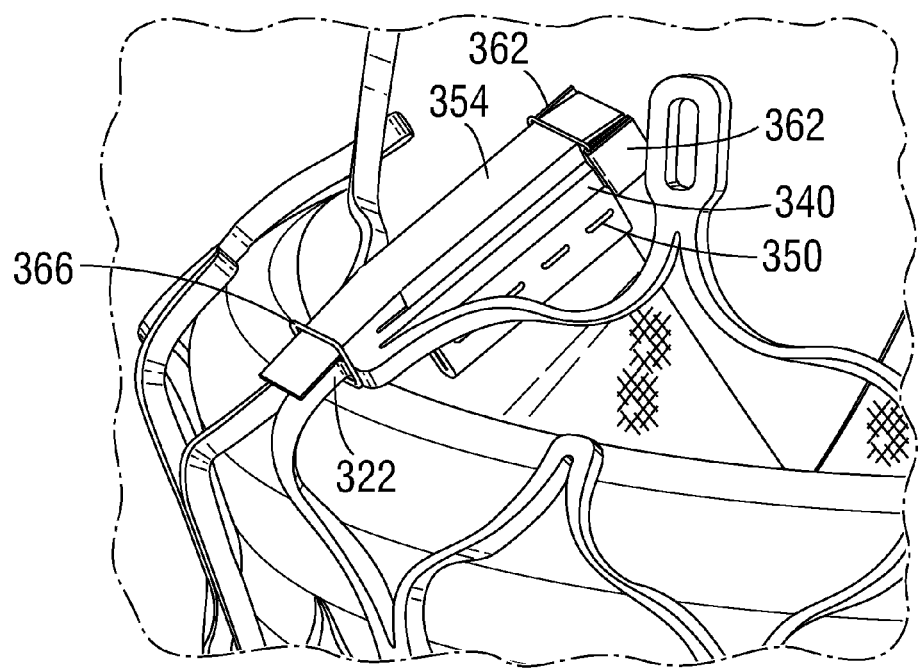
Figure 25:
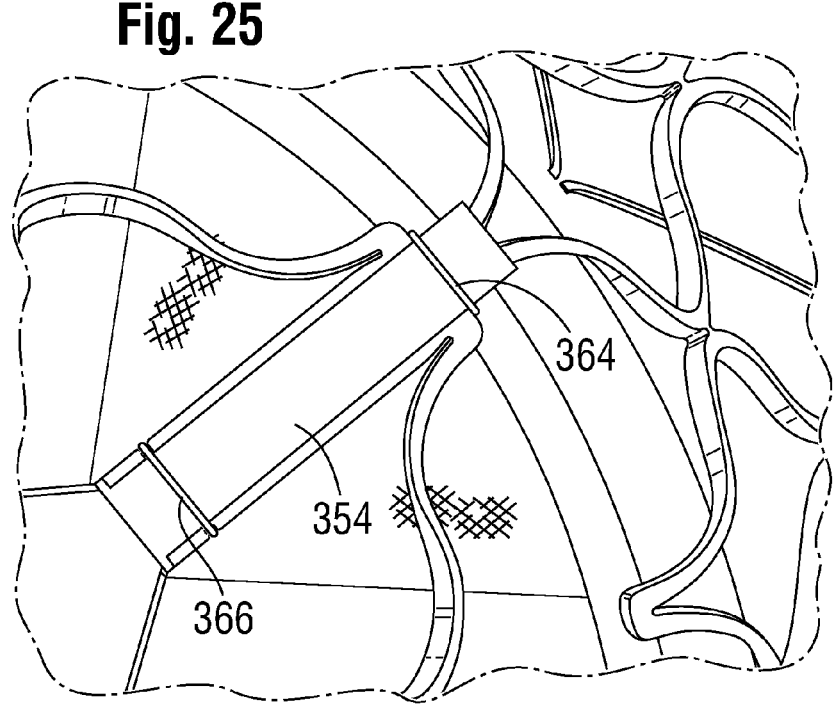

FIG. 20 shows a commissure 330 before a reinforcement portion 352 is placed on and secured to the attachment portion 322. FIG. 21 shows a reinforcement portion 352 in an unfolded configuration prior to being placed on and secured to an attachment portion 322. The reinforcement portion 352 can be folded partially around a pair of tab portions 334 to form a rear portion 354 (FIGS. 24-25) that extends along the radial outside surface of the commissure attachment portion 322. Extending from the longitudinal edges of the rear portion 354 are side flaps 356*a*, 356*b*. As best shown in FIG. 23, side flap 356*a* extends between leaflet fold 346*a* and an adjacent outer strut 340 and side flap 356*b* extends between leaflet fold 346*b* and an adjacent outer strut 340. As best shown in FIG. 22, a top flap 358 extends from the upper edge of the rear portion 354 and covers the top of the commissure attachment portion 322. A front flap 360 extends downwardly from the front edge of the top flap and covers the portion of the commissure attachment portion 322 above the leaflets. Two upper side flaps 362 extend downwardly from the upper side edges of the top flap 358 and cover the opposite sides of the commissure attachment portion 322 above the leaflets. As best shown in FIG. 24, each of the side flaps 362 can be a double layer comprising an inner fold and an outer fold.

The leaflet tab portions 334 and the reinforcement portion 352 can be tightly secured to the inner and outer struts 338, 340 by a suture loop 364 (FIG. 23) that is tightened around the upper end portions of the struts 338, 340. Because the struts 338, 340 are cantilevered themselves and unattached to each other at their upper ends, tightening the suture loop 364 draws the struts 338, 340 inwardly toward the longitudinal centerline of the commissure attachment portions 322 (the line equidistant from the inner struts 338), thereby clamping the folds of the leaflets and the reinforcement portion between the struts 338, 340. The suture loop 364 can be located within the notches 344 (FIG. 15A) of the outer struts 340, which prevent the loop 364 from sliding along the length of the struts. Another suture loop 366 (FIGS. 24 and 25) can be tightened around the lower end of the commissure attachment portion 322 and lower end portion of the reinforcement portion 352.

The lower edge 332 of each leaflet 308 can be secured to the skirt 306 along a suture line 368 (FIG. 13). The lowermost sections of the lower edges 332 of the leaflets (indicated by suture line 368) desirably are aligned with the inflow edge of the frame 302. In this manner, the leaflets 308 extend the entire length or substantially the entire length of the frame from the inlet end to the outlet end of the frame. The skirt 306 can be secured directly to the frame 302 with sutures (not shown), in the same manner that skirt 16 (FIG. 1) is secured to the frame 12 with sutures 60.

The process suturing leaflet commissures to a frame is a time-consuming and tedious process. The struts 338, 340 of the commissure attachment portions are advantageous in that they provide a robust attachment for the leaflet tab portions 334 while significantly minimizing the extent of suturing required to secure the leaflet commissures to the frame compared to known techniques. In particular embodiments, for example, only two suture loops 364, 366 are used to secure a reinforcement portion 352 to a commissure attachment portion 322 and to a pair of leaflet tab portions 334, and other than sutures 350*a*, 350*b*, no further stitching is required to secure together multiple folds of the leaflet to each other or to the folds of the reinforcement portion 352.

Another important advantage provided by the commissure attachment portions is that they minimize the amount of leaflet material positioned on the outside of the frame. This reduces friction between the outside of the prosthetic valve and the deliver sheath, such as when the prosthetic valve is deployed from the sheath. Moreover, if the prosthetic valve is retracted back into the sheath after its initial deployment, the prosthetic valve can slide more easily back into the sheath while minimizing the risk of damage to the leaflet material on the outside of the frame that may occur from contact with the distal end of the sheath.

Figure 26:
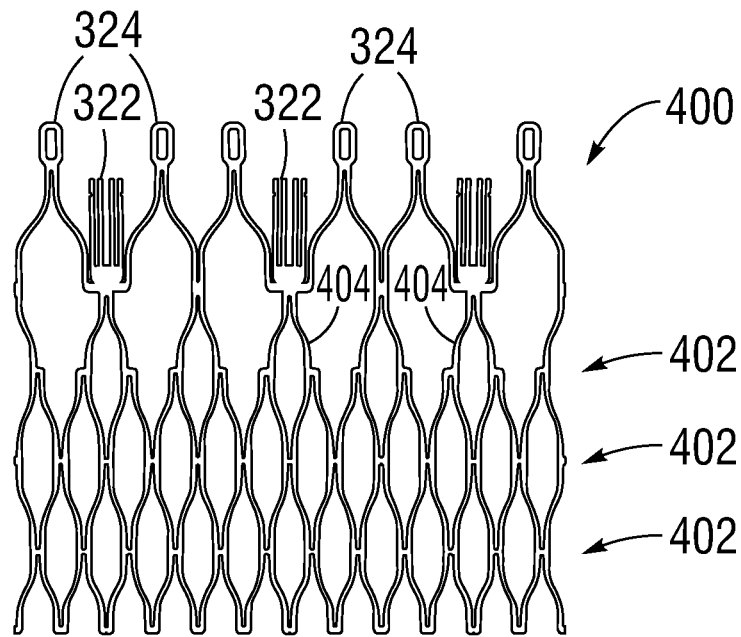
FIG. 26 is a flattened view of another embodiment of a frame that can be used in the prosthetic valve of FIG. 13.

FIG. 26 shows another embodiment of a frame 400 that can be used in the prosthetic valve 300. Frame 400 is similar to frame 302 (FIG. 15), except for the number of cells bridging the intermediate portion 316 and the outflow portion 320. Referring to FIG. 15, except for the uppermost row of cells formed by the retaining arms 324, each row 370 of cells of the frame includes twelve cells 372. Referring to FIG. 26, the uppermost row 402 of cells bridging the intermediate portion 316 and the outflow portion 320 includes six cells 404, which reduces the amount of metal in that portion of the frame. The uppermost row 402 of cells circumscribes the widest portion of the leaflets (except for the tab portions 334) and therefore corresponds to the volume occupied by the bulk of the leaflets when the prosthetic valve is radially crimped. Therefore, the removal of metal from the frame, and in particular from the portion of the frame circumscribing the widest portion of the leaflets, allows for a smaller crimped diameter for the prosthetic valve.

Figure 27:
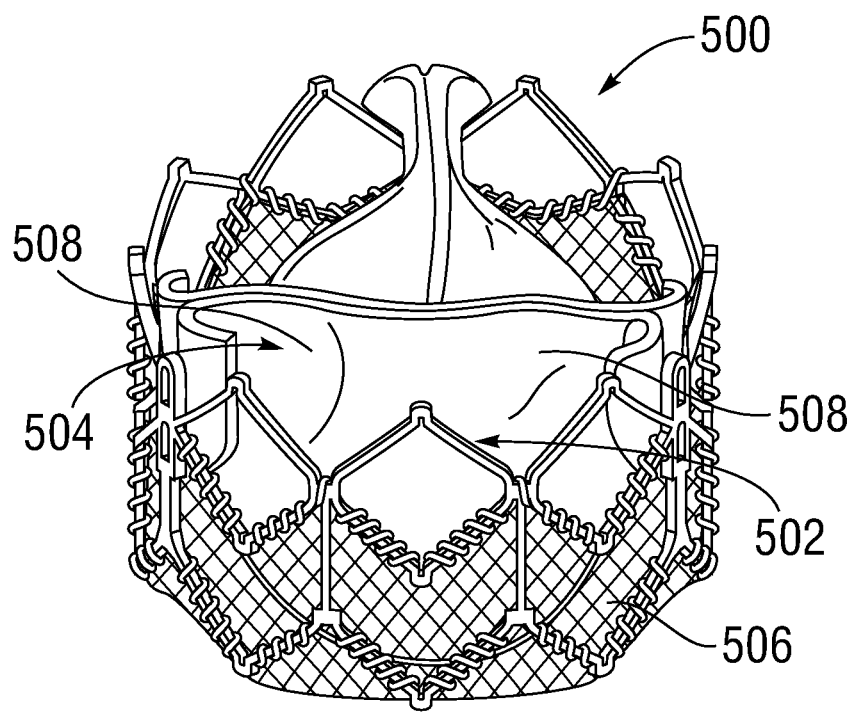
FIG. 27 is a perspective view of a prosthetic heart valve, according to another embodiment.

FIG. 27 illustrates an embodiment of a prosthetic valve 500, which is described in detail in U.S. Pat. No. 7,993,394, which is incorporated herein by reference. The prosthetic valve 500 can have three main components: a stent, or frame, 502, a valvular structure 504, and an inner skirt 506. The prosthetic valve 500 is configured to be radially compressed to a crimped state for delivery into the body of a patient and radially expandable from the crimped state to an expanded state once positioned at the desired implantation location within the body. The valvular structure 504 can comprise three leaflets 508, collectively forming a leaflet structure, which can be arranged to collapse in a tricuspid arrangement, as shown.

Figure 28:
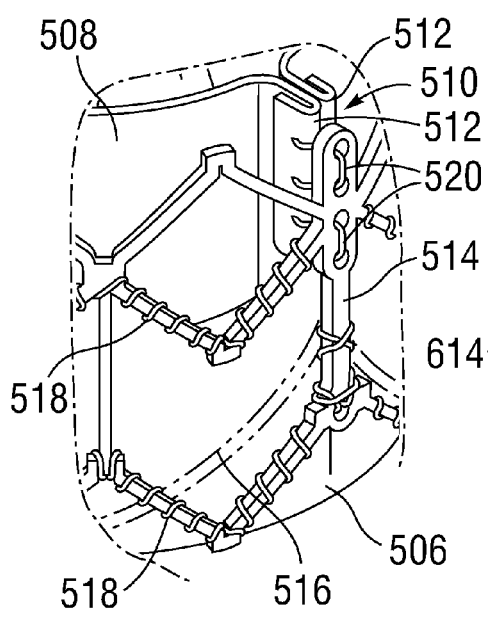
FIG. 28 is an enlarged view of a section of the prosthetic valve of FIG. 27, showing the connection of a commissure to the frame of the valve.

FIG. 28 is an enlarged view of a section of the prosthetic valve 500 showing the connection of a commissure 510 of two adjacent leaflets 508 to the frame. As shown, the commissure 510 is formed by securing a pair of leaflet tab portions 512 to each other and to a commissure attachment post 514 of the frame 502 with sutures 520. The lower edges of the leaflets 508 can be sutured to the skirt 506 along a suture line 516, and the skirt 506 can be secured to the frame 502 with sutures 518.

Figure 29:
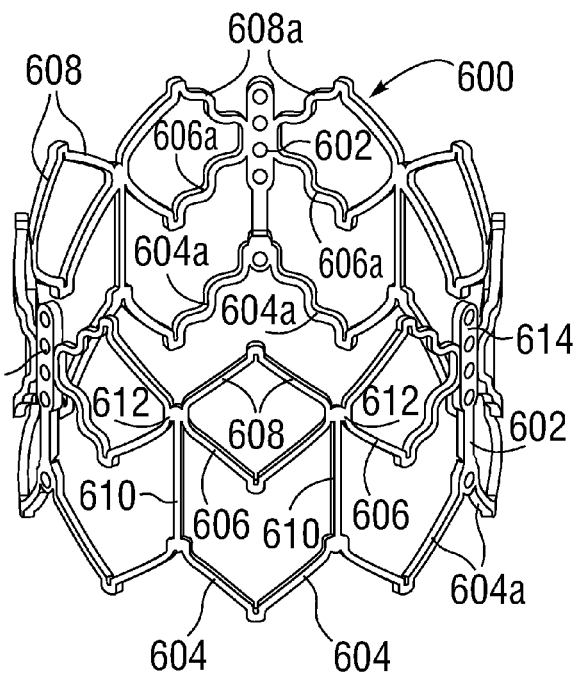
FIG. 29 is a perspective view of another embodiment of a frame that can be used in the prosthetic valve of FIG. 27, showing the frame in an expanded state immediately after deployment by a balloon.

FIG. 29 shows a stent, or frame, 600 according to another embodiment that can be used in the prosthetic valve 500 of FIGS. 27 and 28. In particular embodiments, the frame 600 is a plastically-expandable frame (i.e., is expanded with a balloon or equivalent mechanism) and is configured to undergo post-deployment shaping after being deployed in a patient's body. In particular, the frame 600 in the illustrated configuration is configured to be deployed into a generally cylindrical configuration using a conventional cylindrical balloon, and after deflating and removing the balloon, the commissure attachment portions can bend inwardly to support the commissures of the leaflets at locations closer to the central flow axis of the prosthetic valve. In particular embodiments, a prosthetic valve can comprise the frame 600 and the leaflet structure 304 comprising leaflets 308 of the prosthetic valve 300.

FIG. 29 shows the frame 600 in a radially expanded state after being expanded by an inflatable balloon of a balloon catheter. The balloon can be a conventional balloon that assumes a generally cylindrical shape when inflated. Hence, as depicted in FIG. 29, the frame 600 can assume a generally cylindrical shape when expanded by the balloon. The frame 600 in the illustrated configuration comprises a plurality of commissure attachment posts, or struts, 602 (three in the illustrated embodiment), a first row of struts 604 at the inflow end of the frame, and a second row of struts 606 and a third row of struts 608 at the outflow end of the frame. A plurality of longitudinal struts 610 extend between the apices of the first row of struts 604 and nodes 612 adjoining adjacent cells formed by struts 606 and 608.

The frame 600 is configured to permit inward titling or displacement of the upper portions 614 of the commissure attachment posts 602 when they are first subjected to a closing force of the leaflets under diastolic pressure and then remain in the tilted position. To such ends, struts 606a and 608a that are connected directly to the commissure attachment posts 602 can be weakened relative to the other struts by reducing or thinning the cross-sectional profile of the struts 606a, 608a, such as by reducing the thickness and/or width of the struts 606a, 608a, and by providing one or more curves or bends in the struts 606a, 608a. The curves or bends in the struts 606a, 608a provide slack in those struts to permit the commissure attachment posts 602 to flex inwardly relative to longitudinal struts 610.

Figure 30:
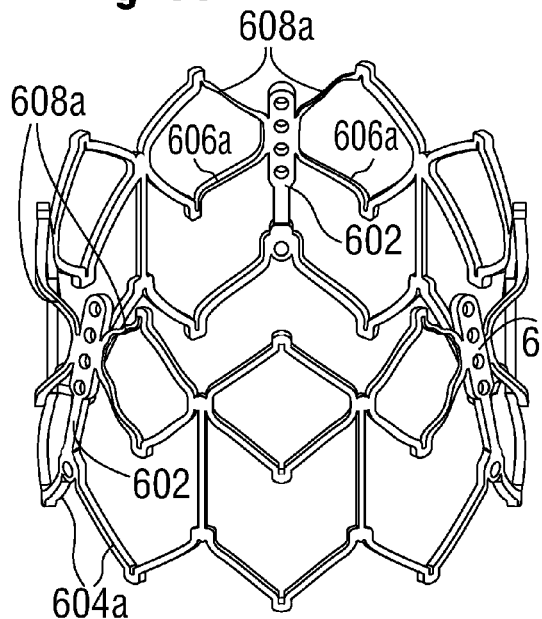
FIG. 30 is a perspective view of the frame of FIG. 29, showing the frame after the commissure posts are displaced by the closing forces of the leaflets.
Figure 31:
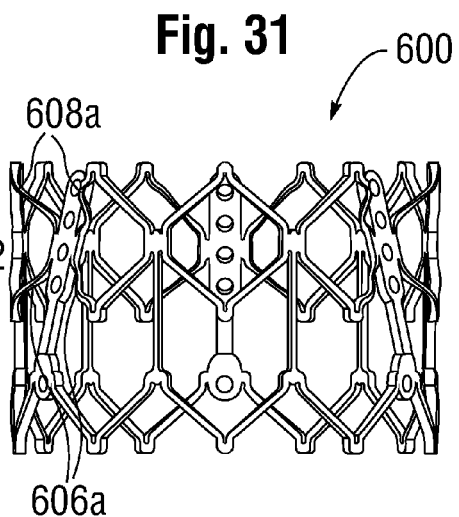
FIG. 31 is a side elevation view of the frame of FIG. 30.

When the prosthetic valve is first deployed within the native aortic valve (or another native heart valve) by inflating a balloon, the frame 600 is expanded to the expanded shape shown in FIG. 29. Upon deflation and removal of the balloon, diastolic pressure causes the leaflets (e.g., leaflets 508) to close, and the closing force of the leaflets draws the upper portions 614 of the commissure attachment posts 602 to bend or tilt inwardly to the positions shown in FIGS. 30 and 31. As the posts 602 are drawn inwardly, the struts 606a, 608a are straightened and limit further bending of the posts 602. The struts 606a, 608a in their straightened or nearly straightened configuration exhibit sufficient rigidity to retain the posts 602 in their titled position under systolic pressure. Thus, after the initial prosthetic valve closing, the posts 602 remain their titled position supporting the commissures (e.g., commissures 510) closer to the longitudinal flow axis of the prosthetic valve. Accordingly, a plastically-expandable valve incorporating the frame 600 can achieve an overall shape similar to that shown in FIGS. 11 and 12 without a specially shaped balloon assembly. The inwardly canted posts 602 support the moveable portions of the leaflets away from the inner surface of the frame 600 when the leaflets are in the open position, thereby protecting the leaflets against abrasion caused by contact between the leaflets and the frame, as previously discussed.

If desired, the struts 604a of the first row that are connected directly to the posts 602 can have a configuration similar to posts 606a, 608a. Weakening the struts 604a connected to the lower ends of posts 602 can facilitate displacement of the posts 602 by allowing for slight outward deflection of the lower ends of the posts 602. In addition, the posts 602 can be weakened at one or more selected locations to facilitate displacement of the posts. As shown in FIGS. 32 and 33, for example, each post 602 can have a slit, or recessed portion, 616 formed in the inner surface of the post at a location just above the first row of struts 604. The recessed portions 616 weakens the posts 602 and function as a pivot for the posts, allowing the posts to more easily bend at the recessed portions 616 when subjected to the force of the initial closing of the leaflets. In addition to or in lieu of the recessed portions 616, the posts 602 can be weakened by reducing the width and/or the thickness of the posts at selected locations to facilitate displacement of the posts.

A modification of the frame 600 is shown in FIG. 34. In this embodiment of the frame 600, tether or wires 618 can be used to limit the extent of inward displacement of the upper end portions of the posts. For example, each post 602 can be connected to a pair of wires 618, each having one end secured to an apex 620 of the third row of struts and another end secured to the upper end portion 614 of the post 602. When the frame is initially expanded and before subjected to the closing force of the leaflets, there is sufficient slack in the wires 618 to allow the posts 602 to bend inwardly. The length of the wires 618 is selected to allow the posts 602 to bend or tilt inwardly a limited amount when subjected to the force of the initial closing of the leaflets. Upon initial closing of the leaflets, the wires 618 are pulled taught and limit the extent to which the upper end portions of the posts 602 can be pulled inwardly by the force of the leaflets.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic valve comprising:
 a radially collapsible and expandable annular frame, the frame having a plurality of angularly spaced commissure attachment portions and a plurality of lobed portions extending between the commissure attachment portions, such that the commissure attachment portions and the plurality of lobed portions each cross a first plane perpendicular to a longitudinal axis of the frame, the frame having an inlet end and an outlet end; and
 a leaflet structure comprising a plurality of leaflets, each leaflet comprising opposing side portions and an upper edge extending between the side portions, wherein each side portion is secured to an adjacent side portion of another leaflet to form commissures of the leaflet structure, each commissure being attached to one of the commissure attachment portions of the frame, the leaflets movable between an open position to allow blood to flow through the prosthetic valve from the inlet end to the outlet end and a closed position to inhibit the flow of blood through the prosthetic valve from the outlet end to the inlet end, wherein the upper edges of the leaflets are spaced radially inwardly of the lobed portions of the frame when the leaflets are in the open position.

2. The prosthetic valve of claim 1, wherein the frame is self-expandable.

3. The prosthetic valve of claim 1, wherein the frame comprises an outflow end portion and an inflow end portion, wherein the outflow end portion defines the commissure attachment portions and the lobed portions, and the inflow portion comprises a conical shape that tapers from the inlet end of the frame to an inlet end of the outflow end portion.

4. The prosthetic valve of claim 1, wherein the upper edge of each leaflet is scalloped.

5. The prosthetic valve of claim 1, wherein the frame is configured such that a distance between adjacent commissure attachment portions remains substantially constant when the lobed portions are compressed radially a predetermined amount.

6. The prosthetic valve of claim 1, wherein the commissure attachment portions are deflectable for flexing inwardly and outwardly relative to the lobed portions of the frame when the leaflets move between the closed and open positions, respectively, during operation of the prosthetic valve.

7. A prosthetic valve comprising:
a radially collapsible and expandable annular frame, the frame comprising an inlet portion and an outlet portion, the outlet portion comprising a plurality of angularly spaced, cantilevered commissure attachment posts extending radially inwardly toward a longitudinal flow axis of the prosthetic valve; and
a leaflet structure comprising a plurality of leaflets, each leaflet comprising opposing side portions, a scalloped upper edge extending between the side portions, and a scalloped lower edge extending between the side portions;
wherein each side portion is secured to an adjacent side portion of another leaflet to form commissures of the leaflet structure, each commissure being attached to one of the commissure attachment posts, the leaflets movable between an open position to allow blood to flow through the prosthetic valve from the inlet portion to the outlet portion and a closed position to inhibit the flow of blood through the prosthetic valve from the outlet portion to the inlet portion, wherein the upper edges of the leaflets are spaced radially inwardly of the outlet portion of the frame when the leaflets are in the open position such that a gap is formed between the upper edge of each leaflet and the outlet portion of the frame.

8. The prosthetic valve of claim 7, wherein a section of the lower edge of each leaflet extends to a location proximate an inlet end of the frame.

9. The prosthetic valve of claim 7, further comprising an annular skirt positioned inside of and secured to the frame, the lower edge of each leaflet being secured to the skirt.

10. The prosthetic valve of claim 7, wherein the frame comprises an intermediate portion between the inlet portion and the outlet portion, the intermediate portion having an enlarged inlet end of a first diameter, a middle section having a second diameter less than the first diameter, and an enlarged outlet end of a third diameter greater than the second diameter.

11. The prosthetic valve of claim 10, wherein the first diameter is the same as the third diameter.

12. The prosthetic valve of claim 11, wherein the middle section is cylindrical.

13. The prosthetic valve of claim 7, wherein the frame comprises a plurality of struts connected to each other to define a plurality of cells arranged in rows connected to each other along the length of the frame, the commissure attachment posts extending from cells of one of the rows proximate the outflow end of the frame.

14. A prosthetic valve comprising:
a radially collapsible and expandable annular frame, the frame having a plurality of angularly spaced commissure attachment posts, each commissure attachment post comprising at least two cantilevered struts spaced apart from each other to define a leaflet-receiving gap; and
a leaflet structure comprising a plurality of leaflets, each leaflet comprising opposing side portions and an upper edge extending between the side portions, wherein each side portion is secured to an adjacent side portion of another leaflet to form commissures of the leaflet structure, each commissure extending through the leaflet-receiving gap of a respective commissure attachment post, wherein the struts of the commissure attachment post are compressed toward each to clamp the commissure between the struts.

15. The prosthetic valve of claim 14, further comprising a suture tightened around the struts of each commissure attachment post, thereby causing the struts to clamp the commissure between the struts.

16. The prosthetic valve of claim 14, wherein the at least two cantilevered struts of each commissure attachment post comprises two inner struts and two outer struts, a first leaflet receiving gap defined between the inner struts, a second leaflet-receiving gap defined between an inner struts and an adjacent outer strut, and a third leaflet-receiving gap define between the other inner strut and an adjacent outer strut, the side portions forming a commissure extending through the first leaflet-receiving gap with one of the side portions forming a fold extending into the second leaflet-receiving gap and the other of the side portions forming a fold extending into the third leaflet-receiving gap.

17. The prosthetic valve of claim 14, wherein the commissure attachment posts extend radially inwardly toward a longitudinally flow axis of the prosthetic valve.

18. A prosthetic valve comprising:
a radially collapsible and expandable annular frame, the frame being plastically expandable and comprising a plurality of angularly spaced commissure attachment posts; and
a leaflet structure comprising a plurality of leaflets, each leaflet comprising opposing side portions, wherein each side portion is secured to an adjacent side portion of another leaflet to form commissures of the leaflet structure, each commissure being attached to one of the commissure attachment posts;
wherein the commissure attachment posts are configured to deflect radially inwardly toward a longitudinal flow axis of the prosthetic valve when first subjected to closing forces of the leaflets immediately following implantation of the prosthetic valve and wherein the commissure attachment posts remain in a deflected position during subsequent closing and opening cycles of the prosthetic valve.

19. The prosthetic valve of claim 18, wherein the commissure attachment posts, in the deflected position, are configured to retain the upper edges of the leaflets at a position spaced radially inwardly of the frame when the leaflets are in the open position such that a gap is formed between the upper edge of each leaflet and the frame.

20. The prosthetic valve of claim 18, wherein the frame comprises a row of a plurality of angled struts interconnecting the commissure attachment posts at an outflow end of the frame, the plurality of struts comprising struts connected directly to the commissure attachment posts and struts that are not connected directly to the commissure attachment posts, the struts that are connected directly to the commissure attachment posts being relatively more flexible than the struts that are not connected directly to the commissure attachment posts.

* * * * *